(12) United States Patent
Bibian et al.

(10) Patent No.: US 11,553,869 B1
(45) Date of Patent: *Jan. 17, 2023

(54) MULTI-CHANNEL BRAIN OR CORTICAL ACTIVITY MONITORING AND METHOD

(71) Applicants: Stéphane Bibian, Cleveland Heights, OH (US); Tatjana Zikov, Cleveland Heights, OH (US)

(72) Inventors: Stéphane Bibian, Cleveland Heights, OH (US); Tatjana Zikov, Cleveland Heights, OH (US)

(73) Assignee: NeuroWave Systems Inc., Cleveland, OH (US)

( * ) Notice: Subject to any disclaimer, the term of this patent is extended or adjusted under 35 U.S.C. 154(b) by 281 days.

This patent is subject to a terminal disclaimer.

(21) Appl. No.: 15/867,769

(22) Filed: Jan. 11, 2018

Related U.S. Application Data

(63) Continuation of application No. 14/330,408, filed on Jul. 14, 2014, now abandoned, which is a continuation of application No. 12/628,568, filed on Dec. 1, 2009, now Pat. No. 8,838,226.

(51) Int. Cl.
*A61B 5/0476* (2006.01)
*A61B 5/369* (2021.01)
*A61B 5/00* (2006.01)
*A61M 5/172* (2006.01)

(52) U.S. Cl.
CPC .......... *A61B 5/369* (2021.01); *A61B 5/4064* (2013.01); *A61B 5/4082* (2013.01); *A61B 5/4821* (2013.01); *A61B 5/6843* (2013.01); *A61M 5/1723* (2013.01); *A61B 5/7203* (2013.01);

(Continued)

(58) Field of Classification Search
CPC ..... A61B 5/048; A61B 5/4821; A61B 5/7257; A61B 5/0476; A61B 5/4094; A61B 5/4088
See application file for complete search history.

(56) References Cited

U.S. PATENT DOCUMENTS 4,412,547 A * 11/1983 Callahan ............ A61B 5/04014
600/544
4,533,346 A * 8/1985 Cosgrove, Jr. ...... G06F 19/3468
604/66

(Continued)

*Primary Examiner* — Allen Porter
*Assistant Examiner* — Michael A Catina
(74) *Attorney, Agent, or Firm* — Brian Kolkowski

(57) ABSTRACT

The present invention relates to a quantitative electroencephalogram (QEEG) monitor and system capable of monitoring and displaying simultaneously neuropathological characteristic and activity of both sides of a subject's brain. The methods include various indices and examination of differences in these indices by which neurophysiological conditions or problems can be identified and treated. These methods, and the systems and devices using these methods preferably can be used for identifying these neurophysiological conditions or brain dysfunction with monitors and methods for seizure detection, for sedation monitoring, for anesthesia monitoring, and the like. These bilateral brain monitoring methods and systems, and the devices using these methods can be used by individuals or clinicians with little or no training in signal analysis or processing. These bilateral monitoring methods can also be used in a range of applications.

15 Claims, 12 Drawing Sheets

(52) U.S. Cl.
    CPC ............ *A61B 5/726* (2013.01); *A61B 5/7221* (2013.01); *A61B 5/7225* (2013.01); *A61B 5/7257* (2013.01)

(56) References Cited

U.S. PATENT DOCUMENTS

| | | | | |
|---|---|---|---|---|
| 6,950,698 B2* | 9/2005 | Sarkela | ................... | A61B 5/291 |
| | | | | 600/544 |
| 2004/0267153 A1* | 12/2004 | Bergethon | ........... | A61B 5/0484 |
| | | | | 600/554 |
| 2009/0326406 A1* | 12/2009 | Tan | ......................... | G06F 1/163 |
| | | | | 600/546 |
| 2010/0056945 A1* | 3/2010 | Holmes | .................... | A61B 5/01 |
| | | | | 600/549 |

* cited by examiner

MULTI-CHANNEL BRAIN OR CORTICAL ACTIVITY MONITORING AND METHOD

BACKGROUND OF THE INVENTION

1. Field of the Invention

The present invention relates to processing, monitoring and display of signals, and particularly to the processing, monitoring and display of electrophysiological signals. More particularly, the present invention relates to the processing, monitoring and display of electroencephalography (EEG) signals representing cortical/brain activity. Further, the present invention relates to a method and apparatus for displaying separate electrophysiological signals and quantitative process parameters based on these signals and representing the cortical or brain activity of each of the subject's brain hemispheres on the same screen, simultaneously. Even further, the present invention, while displaying cortical or brain activity signals, relates to methods for measuring signal quality, detecting neuropathological activity in the subject, and detecting changes in subject's status.

2. Technology Review

Quantitative electroencephalograph (QEEG) monitoring is a valuable non-invasive tool for monitoring brain activity and detecting numerous forms of neuropathological activity such as seizure and stroke. However, traditional QEEG monitoring techniques focus on the subject's brain as a whole, looking at cortical/brain activity. While this type of monitoring is very useful and even necessary to detect certain neuropathological activity or for certain procedures, such as measuring subject status with respect to sedation or anesthesia or reaction to noxious stimulation such as surgical stimulation, detecting seizures during the monitoring procedure, or detecting brain damage, it cannot always detect other problems or conditions that may arise or exist within one particular brain hemisphere or as a function of the communication between the two brain hemispheres.

These problems may include varying levels of sedation between hemispheres; seizure or stroke related to one side of the brain; or other neuropathological problems. While bilateral brain monitoring methods have been proposed and even utilized for basic monitoring of a subject's two brain hemispheres individually and simultaneously, the focus of such existing methods has been solely based on the patient's state of consciousness by means of brain/cortical activity and this activity circuitously is based on the whole brain rather than the activity of each hemisphere. These methods have ignored the potential for essentially real-time detection of presently occurring neuropathological activity or of the diagnosis or identification and location of such past neuropathological activity particularly where the differences between hemispheric activity is indicative of such problems.

It is therefore an object of the present invention to provide a device, system, monitor and method that meets all of these needs and others where such a device and method is applicable. It is another object of the present invention that this device and method accurately detect and display information simultaneously regarding a subject's brain activity or cortical state and potential neuropathological activity for both hemispheres of the subject's brain. It is still another object of the present invention that this device and method be usable by technicians, clinicians, caregivers, emergency response technicians, or anyone else with appropriate specialized medical training to monitor a subject's brain or cortical activity as well as by such persons with little specialized training but in the position to monitor a subject for neuropathological activity that may occur. Finally, it is an object of the present invention that this device that a patient's diagnosis and therapeutic treatment be more accurately determined based on the better diagnostic data from the testing and monitoring of the patient.

SUMMARY OF THE INVENTION

The present invention relates to a physiological monitor and system, more particularly to a quantitative electroencephalogram (QEEG) monitor and system, even more particularly to a QEEG monitor and system capable of monitoring and displaying signals from each brain hemisphere separately and simultaneously or substantially so to determine underlying neurophysiological problems or also problems related to the measuring device and system.

Bilateral QEEG signal monitoring is a method for the individual, and essentially simultaneous monitoring, measuring, and displaying of EEG activity for each hemisphere of a subject's brain, as well as for the calculation and display of a QEEG index relating to brain or cortical activity and corresponding to the level of activity in each of those brain hemispheres. By examining differences in the indices corresponding to each of those brain hemispheres neurophysiological conditions and/or other problems can be identified and treated. These methods may also be used similarly with the quantification of other physiological signals such as electrooculography (EOG), electromyography (EMG), electrocardiography (ECG), electrical impedance tomography (EIT), and the like.

These methods, and the systems and devices using these methods preferably can be used for identifying these neurophysiological conditions or brain dysfunction with monitors and methods for seizure detection, for sedation monitoring, for anesthesia monitoring, and the like. Preferably, these methods, systems and devices can be used in operating rooms, during acute care such as in intensive care units, or in critical care such as the emergency rooms or in the field. These methods, systems and devices can be used by anesthesiologists, nurse anesthetists, neurologists and neurosurgeons, pulmonologists, emergency room physicians and clinicians, intensive care physicians and clinicians, medics, paramedics, emergency medical technicians, respiratory technicians, and the like. Preferably, these methods, systems, and devices using these methods can be used by individuals or clinicians with little or no training in signal analysis or processing. These methods preferably are used with anesthesia monitors, seizure detectors, sedation monitors, sleep diagnostic monitors, any sort of EEG monitor, battlefield monitors, operating room monitor, ICU monitor, emergency room monitor, any other sort of ECG monitor, and the like.

The various embodiments of the system of the present invention were developed for monitoring and processing various physiological signals from a subject. Preferably, this system is used for the brain wave or activity monitoring of a single patient or multiple patients. Preferably, the system is a multi-electrode EEG system; however, depending on purpose of use and cost, systems may have as few as 3 electrodes: with at least 2 electrodes for measurement of brain or cortical activity, one for each hemisphere of the subject's rain, and at least one reference electrode. Preferably, the system or monitor of the present invention also includes one or more methods or algorithms for detecting or quantifying brain or cortical activity, and/or level of consciousness, seizure detection, level of sedation and the like. Preferably, the system or monitor can also measure muscle activity, EMG and EOG, contained in the EEG signal, as well as other spectral components of the EEG signal. These components may include but are not limited to the suppression ratio which is the ratio of time where there is no substantial brain or cortical activity to the time where there is cortical or brain activity shown in the EEG signal and burst count which is the number of high frequency bursts. In addition, the system and related methods can use other sensors that measure physiological signals which directly or indirectly result in or from brain dysfunction, or effect or result from brain activity.

Preferably, the system or monitor is constructed to be rugged, so as to withstand transport, handling and use in all of the applications listed above including in emergency scenarios, such as on the battlefield or in mass casualty situations, or to reliably survive daily use by emergency medical personnel or other first responders. The system or monitor should preferably be splash-proof (or water tight), dust-tight, scratch-resistant, and resistant to mechanical shock and vibration. The system or monitor should preferably be portable and field-deployable in particular embodiments to a military theater of operation, the scene of an accident, the home of a patient, or to any clinical setting.

The system or monitor should preferably be capable of non-expert use. By this, it is meant that a person should not be required to possess extraordinary or special medical training in order to use the system effectively and reliably. The system should therefore preferably be automatic in operation in a number of respects. First, the system should be capable of automatic calibration. Second, the system should preferably have automatic detection of input signal quality; for example, the system should be capable of detecting an imbalance in electrode impedances, physiological and environmental artifacts, and electrical interferences and noise. Third, the system should preferably be capable of artifact detection and removal on one or more levels, so as to isolate for analysis that part of the signal which conveys meaningful information related to a subject's brain or cortical activity, level of consciousness, occurrence of a seizure, level of sedation and the like. Fourth, the system should preferably include outputs which result in visual and/or audible feedback capable of informing the user of the state of the patient related to quantification of brain or cortical activity, level of consciousness, occurrence of a seizure, level of sedation and the like at any time during the period of time that the system was monitoring the patient.

Preferably, the system should operate in real time. One example of real-time operation is the ability of the system to detect a seizure or brain dysfunction event as it is happening, rather than being limited to analysis that takes place minutes or hours afterward.

The processor or computer, and the methods of the present invention preferably contain software or embedded algorithms or steps that automatically identify artifacts and even more preferably remove the artifacts from the physiological signal, and automatically quantify brain or cortical activity, level of consciousness, identify seizures or other brain dysfunction, level of sedation based on the essentially artifact free EEG signal.

The system described in this invention also preferably incorporates a number of unique features that improve safety, performance, durability, and reliability. The system should be cardiac defibrillator proof, meaning that its electrical components are capable of withstanding the surge of electrical current associated with the application of a cardiac defibrillator shock to a patient being monitored by the system, and that the system remains operable after sustaining such a surge. The system should have shielded leads so as to reduce as much as possible the effects of external electromagnetic interference on the collection of biopotential or physiological signals from the patient being monitored by the system. The system should be auto-calibrating, more preferably capable of compensating for the potential differences in the gains of the input electrodes to the patient module. The system should be capable of performing a continuous impedance check on its electrode leads to ensure the suitability of monitored signals.

One embodiment of the present invention is a method of determining EEG signal quality in a device for quantifying brain or cortical activity during sedation or anesthesia comprising steps of monitoring a subject with a brain having a left hemisphere and a right hemisphere, by hooking the subject up to a brain or cortical activity quantification device with at least two measurement electrodes, and at least one reference electrode, the at least two measurement electrodes comprising at least one EEG electrode, having a signal, positioned to monitor left hemisphere brain or cortical activity and at least one EEG electrode, having a signal, positioned to monitor right hemisphere brain or cortical activity of the subject's brain, the reference electrode comprising at least one EEG electrode, each electrode providing an EEG signal to a processor, measuring the brain or cortical activity of both the subject's left and right brain hemispheres essentially simultaneously, calculating with the processor corresponding indices relating to the brain or cortical activity of both the left and right hemisphere of the subject's brain, transmitting the indices from the processor to a monitor, displaying both of the indices on a monitor simultaneously, comparing the indices of each hemisphere's cortical activity, and determining whether the signal of at least one of the EEG electrodes is likely to have too high of an impedance. Input signal quality can be affected by an imbalance in electrode impedances, physiological and environmental artifacts, and electrical interferences and noise, among other factors, and the calculated QEEG indices can be used to display these factors.

Another embodiment of the present invention is a method of detecting neuropathological activity with a device for quantifying brain or cortical activity in a subject during sedation or anesthesia comprising the steps of monitoring a subject with a brain having a left hemisphere and a right hemisphere, by hooking the subject up to a brain or cortical activity quantification device with at least two measurement electrodes, and at least one reference electrode, the at least two measurement electrodes comprising at least one EEG electrode, having a signal, positioned to monitor left hemisphere brain or cortical activity and at least one EEG electrode, having a signal, positioned to monitor right hemisphere brain or cortical activity of the subject's brain, the reference electrode comprising at least one EEG electrode, each electrode providing an EEG signal to a processor, measuring the brain or cortical activity of both the subject's left and right brain hemispheres essentially simultaneously, calculating with the processor corresponding indices relating to the brain or cortical activity of both the left and right hemisphere of the subject's brain, transmitting the indices from the processor to a monitor, displaying both of the indices on a monitor simultaneously, comparing the indices of each hemisphere's cortical activity, and determining whether the brain or cortical activity of one hemisphere of the brain is indicative of a neuropathological condition when compared to the brain or cortical activity of the other hemisphere of the brain of the subject.

Still another embodiment of the present invention is a method of detecting a sudden change in subject status with a device for quantifying brain or cortical activity in the subject during sedation or anesthesia comprising the steps of monitoring a subject with a brain having a left hemisphere and a right hemisphere, by hooking the subject up to a brain or cortical activity quantification device with at least two measurement electrodes, and at least one reference electrode, the at least two measurement electrodes comprising at least one EEG electrode, having a signal, positioned to monitor left hemisphere brain or cortical activity and at least one EEG electrode, having a signal, positioned to monitor right hemisphere brain or cortical activity of the subject's brain, the reference electrode comprising at least one EEG electrode, each electrode providing a EEG signal to a processor, measuring the brain or cortical activity of both the subject's left and right brain hemispheres essentially simultaneously, calculating with the processor corresponding indices relating to the brain or cortical activity of both the left and right hemisphere of the subject's brain. transmitting the indices from the processor to a monitor, displaying both of the indices on a monitor simultaneously, comparing the indices of each hemisphere's cortical activity, and determining whether the brain or cortical activity of one hemisphere of the brain is indicative of a change in subject status when compared to the brain or cortical activity of the other hemisphere of the brain of the subject. This change in subject status can be a change in level of wakefulness or awareness, or a reaction to noxious or surgical stimulation.

Yet another embodiment of the present invention is a method of performing closed-loop anesthesia or sedation to a subject with a device for quantifying brain or cortical activity comprising the steps of monitoring a subject with a brain having a left hemisphere and a right hemisphere, by hooking the subject up to a brain or cortical activity quantification device with at least two measurement electrodes, and at least one reference electrode, the at least two measurement electrodes comprising at least one EEG electrode, having a signal, positioned to monitor left hemisphere brain or cortical activity and at least one EEG electrode, having a signal, positioned to monitor right hemisphere brain or cortical activity of the subject's brain, the reference electrode comprising at least one EEG electrode, each electrode providing a EEG signal to a processor, measuring the brain or cortical activity of both the subject's left and right brain hemispheres essentially simultaneously, calculating with the processor corresponding indices relating to the brain or cortical activity of both the left and right hemisphere of the subject's brain, transmitting the indices from the processor to a monitor, displaying both of the indices on a monitor simultaneously, comparing the indices of each hemisphere's cortical activity, and determining the subject's need for additional anesthetic or sedation based on a least risk approach calculated by comparing the indices of each hemisphere's cortical activity.

Yet another embodiment of the present invention is a method of providing a message to the user of the device for quantifying brain or cortical activity during sedation or anesthesia comprising steps of monitoring a subject with a brain having a left hemisphere and a right hemisphere, by hooking the subject up to a brain or cortical activity quantification device with at least two measurement electrodes, and at least one reference electrode, the at least two measurement electrodes comprising at least one EEG electrode, having a signal, positioned to monitor left hemisphere brain or cortical activity and at least one EEG electrode, having a signal, positioned to monitor right hemisphere brain or cortical activity of the subject's brain, the reference electrode comprising at least one EEG electrode, each electrode providing a EEG signal to a processor, measuring the brain or cortical activity of both the subject's left and right brain hemispheres essentially simultaneously, calculating with the processor corresponding indices relating to the brain or cortical activity of both the left and right hemisphere of the subject's brain, comparing with a processor the indices of each hemisphere's cortical activity, and displaying a message, either audible or visual, or a combination thereof, notifying a technician, physician, caregiver, or other user that some attention is needed by the patient and/or brain or cortical activity quantification device.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. It is understood that many other embodiments of the invention are not directly set forth in this application but are none the less understood to be incorporated by this application. The accompanying drawings are included to provide a further understanding of the invention, and are incorporated in and constitute a part of this specification. The drawings illustrate various embodiments of the invention and together with the description serve to explain the principles and operation of the many embodiments of this invention.

DETAILED DESCRIPTION OF THE DRAWINGS

Figure 1:
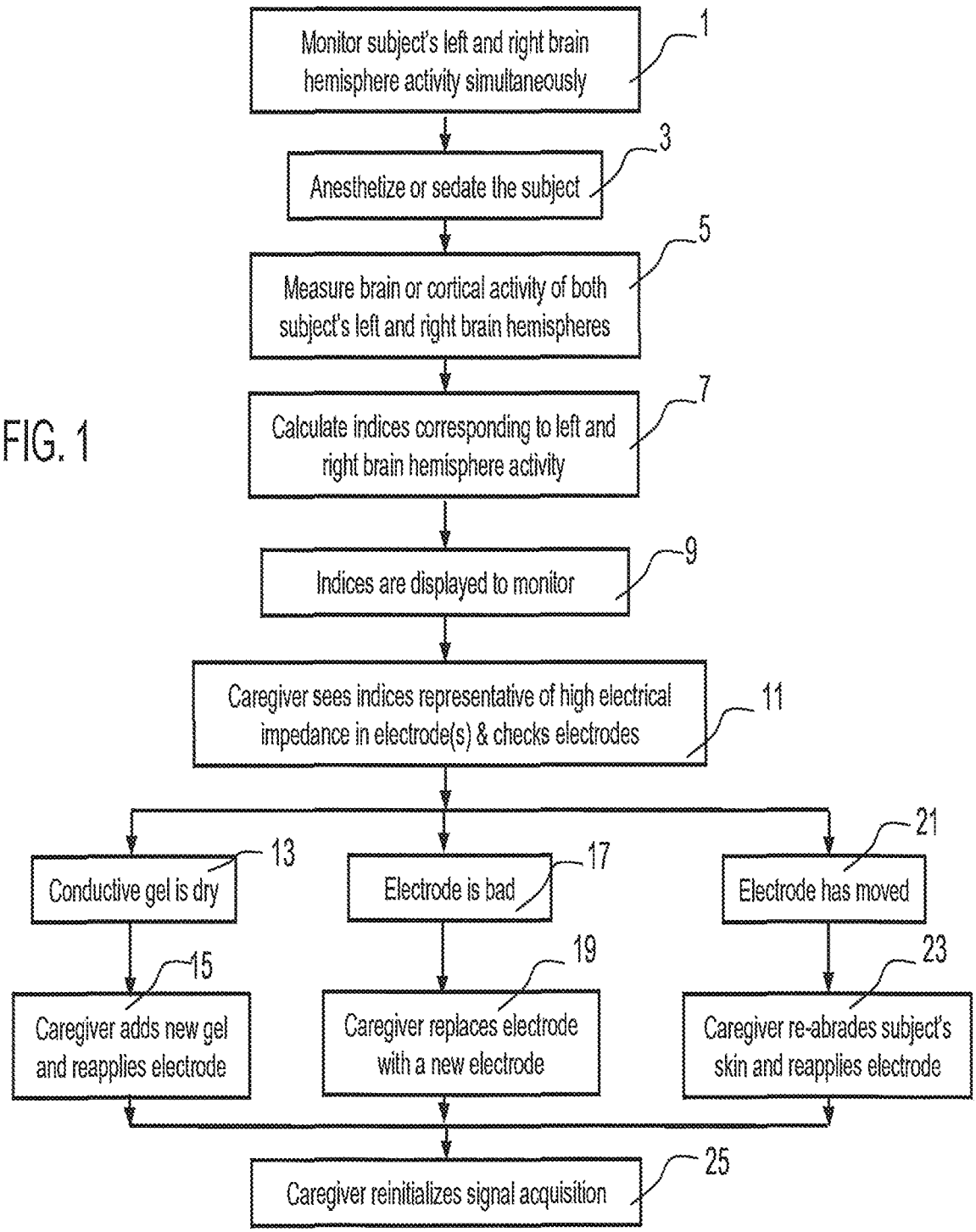
FIG. 1. Flowchart depicting a process of detecting signal quality.

The present invention relates to a physiological monitor and system, more particularly to an electroencephalogram (EEG) monitor and system, even more particularly to a QEEG (quantitative electroencephalogram) monitor and system capable of monitoring and displaying signals from each brain hemisphere separately and simultaneously.

For the present invention the subject whose EEG signal is being measured can be any type of animal, preferably a mammal, most preferably a human. Also, caregiver is understood to include not only those skilled in the use of EEG equipment and methodologies, such as doctors, physicians, anesthesiologists, EEG technologists, emergency response personnel, nurses, and the like, but also home care individuals, such as family members or other non-medically trained persons who may be responsible for caring for individuals in need of such equipment at home with minimal additional training.

Various embodiments of the methods of the present invention include one or more of the following steps, and variations thereof. These steps include monitoring a subject with a brain having a left hemisphere and a right hemisphere, by hooking the subject up to a brain or cortical activity quantification device with at least two measurement electrodes, and at least one reference electrode, the at least two measurement electrodes comprising at least one EEG electrode, having a signal, positioned to monitor left hemisphere brain or cortical activity and at least one EEG electrode, having a signal, positioned to monitor right hemisphere brain or cortical activity of the subject's brain, the reference electrode comprising at least one EEG electrode, each electrode providing an EEG signal to a processor.

This step includes using at least one sensor to measure a subject's brain wave signals over a period of time. The brain wave or EEG signals can be obtained by any method know in the art, or subsequently developed by those skilled in the art to detect these types of signals. Sensors include but are not limited to electrodes or magnetic sensors. Since brain wave signals are, in general, electrical currents which produce associated magnetic fields, the present invention further anticipates methods of sensing those magnetic fields to acquire brain wave signals similar to those which can be obtained through for example an electrode applied to the subject's scalp. The subject(s) referred to in the present invention can be any form of animal. Preferably the subject(s) are mammal, and most preferably human.

If electrodes are used to pick up the brain wave signals, these electrodes may be placed at one or several locations on the subject(s)' scalp. The electrode(s) can be placed at various locations on the subject(s) scalp in order to detect EEG or brain wave signals. Common locations for the electrodes include frontal (F), parietal (P), anterior (A), central (C) and occipital (O).

In order to obtain a good EEG or brain wave signal it is desirable to have low impedances for the electrodes. Typical EEG electrodes connections may have impedance in the range of from 5 to 10 K ohms. It is, in general, desirable to reduce such impedance levels to below 2 K ohms. Therefore a conductive paste or gel may be applied to the electrode to create a connection with impedance below 2 K ohms. Alternatively, the subject(s) skin may be mechanically abraded, the electrode may be amplified or a dry electrode may be used. Dry physiological recording electrodes of the type described in U.S. Pat. No. 6,785,569 can be used. U.S. Pat. No. 6,785,569 is hereby incorporated by reference. Dry electrodes provide the advantage that there is no gel to dry out, no skin to abrade or clean, and that the electrode can be applied in hairy areas such as the scalp.

Additionally if electrodes are used as the sensors, preferably at least three electrodes are used—one measurement electrode for an EEG signal from the subject's left brain hemisphere, one measurement electrode for an EEG signal from the subject's right brain hemisphere, and one reference electrode; and if further EEG or brain wave signal electrodes are desired the number of electrodes required will depend on whether separate reference electrodes or a single reference electrode is used. Each desired electrode of EEG signal requires two measurement electrodes, one for each brain hemisphere. For the various embodiments of the present invention, preferably an electrode is used and the placement of at least one of the electrodes is at or near the occipital lobe of the subject's scalp.

Preferably, the physiological electrodes or other sensors are placed on the subject's head with at least one measurement electrode on each side of the subject's head (i.e. left and right sides as divided by the sagittal physiological plane). Also preferably, at least one reference electrode needs to be placed in order to obtain and measure the differential EEG signals from each of the measurement electrodes. In order to be able to compare the signals from the left and right hemispheres of the subject's brain, the reference electrode is preferably placed as close as possible to the center of the subject's head. This placement should coincide with the location of the longitudinal fissure. When placed as close to the longitudinal fissure as possible, the reference electrode will receive EEG signals from both hemispheres of the subject's brain, and therefore produces a common signal that can be used to create accurate and comparable differential calculations between the EEG signals measured from each individual brain hemisphere.

Though the measurement electrodes can be placed in any position on the subject's head where they are able to distinguish between EEG signals from specific hemispheres of the subject's brain, the electrodes are most preferably placed in a symmetrical pattern. A symmetrical electrode array can be used to provide this symmetrical pattern. If a symmetrical electrode array is used this would allow for placement of electrodes in a manner such that they are in substantially identical placement on either side (a side being the right or left as separated along the sagittal plane of the body) of the subject's head. This means that the electrodes in the array are placed substantially equidistant from the center of the subject's head, or from the longitudinal fissure which is the crevice or separation between the left and right hemispheres of the brain. For example, if a measurement electrode is placed on the left side of the subject's head, on the left temple, next to the left eye, in order to measure EOG activity, then likewise a measurement electrode should be placed on the right side of the subject's head, on the right temple, next to the right eye. As with the above non-symmetrical electrode placement technique, at least one reference electrode is preferably placed on the subject's head, as near to the longitudinal fissure or center of the subject's head along the sagittal plane, as possible.

If an electrode array is used, preferably the array is a 3 electrode array, more preferably a 5 electrode array, and most preferably a 7 electrode array. Electrode arrays with 4 and 6 electrodes and with 2 reference electrodes per array can be used as well. If 2 or more reference electrodes are used these electrodes are placed substantially near or on the sagittal plane of the subject's head.

Once the patient is correctly attached to the EEG monitoring system then each electrode that has been attached to the subject can transmit an EEG signal to the processor. Each of the at least two measurement electrodes transmits a measurement EEG signal which is compared against the corresponding reference electrode signal. These signals are then used to calculate the QEEG index relating to brain or cortical activity for each hemisphere of the subject's brain.

Another step of various embodiments of the present invention includes anesthetizing or sedating the subject. Anesthetization or sedation of the subject occurs according to strict guidelines and calculations for the safe and accurate administering of medication. Anesthetization and sedation techniques that can be used in conjunction with the present invention primarily include the administration of gas, intravenous medication delivery, but also any other methods that may be used.

Anesthesia is the general term for methods of blocking a subject's sensations, primarily of pain (analgesia), and/or movement, as well as memory (amnesia), for the purposes of performing surgical or other medical treatment on a subject. Anesthesia can be general, rendering the subject completely unconscious and blocking sensation over the entire body, or local, which blocks the sensation of just a small area of the body. It is general anesthesia to which the methods of the present invention are concerned. General anesthesia is generally administered via inhalation of anesthetic gas (e.g. Isoflurane, Desflurane, etc.) or intravenous anesthetic (e.g. Propofol, Lorazepam, Midazolam, Thiopental, Diazepam, etc), but other forms of medications that can be given as part of the anesthesia scheme or in conjunction therewith including sedatives, beta-blockers, neuromuscular blockage agents, vaso-constrictors, vaso-dilators and the like are considered as well. Inhaled anesthetics are generally applied by placing an anesthesia mask over the subject's mouth and nose and supplying the anesthetic gas through the mask so the subject inhales it while breathing in until it takes effect and renders the subject unconscious. Intravenous anesthetics are administered by placing an intravenous catheter into the subject, and either injecting the anesthetic via syringe into the injection port of the catheter or attaching a hose from the anesthetic supply to the connecting hub of the catheter and allowing the anesthetic to drip and infuse into the subject's blood stream. Other methods for administering anesthetic medication are also available and can be utilized with the present invention, and future methods developed by those skilled in the art will be applicable to the present invention as well.

Anesthesia serves clear and well-known benefits in the clinical and hospital setting. Patients undergoing surgery are quite often subjected to anesthesia to block the pain arising from the surgical procedures as well as to render them motionless for the purposes of performing the surgical procedures.

Sedation is a process by which a subject is calmed or anxiety is reduced. Sedatives are often used in conjunction with anesthetics to dull pain from medical procedures as sedation does not have an analgesic effect on its own. Similar to the various forms of anesthesia, sedation is commonly obtained through the administering of a sedative via inhalation or intravenous catheter. Common sedatives used in medical procedures include clonazepam, phenobarbitol, and the like.

Sedation is very useful in areas such as the hospital ICU where, relating to the present invention, it is often necessary to keep the patient subdued to monitor brain function as he or she recovers from brain surgery or other injury, or to prevent him or her from fighting the equipment to which he or she is attached, such as a ventilator. In many situations, particularly in the event of brain surgery or injury, EEG monitoring is necessary to ensure that a patient's is recovering and functioning normally. Sedation prevents the patient from becoming agitated and interfering with the EEG monitoring process by moving excessively or by removing the monitoring sensors. Additionally, patients often are required to use ventilators to assist in breathing and many find ventilator tubes to be very uncomfortable and even painful, and are very prone to pulling or yanking the tubes out, despite the fact that they will likely have trouble breathing without it. Sedating the patient helps to alleviate their discomfort (if combined with an analgesic agent) or simply tranquilizes them so they cannot pull at the tubes and cause themselves further harm. Further, patients on ventilators often instinctively "fight" the ventilator, which is they attempt to breath in a different pattern than that set by the ventilator causing anxiety or panic with the patient. Many times a patient is over sedated in order to prevent this anxiety or panic. Over sedating the patient results in higher infection rates as well as longer periods of time necessary to wean the patient from the ventilator.

Another situation where anesthesia and/or sedation are required is during artificially induced coma. Severe brain trauma and neurosurgery are circumstances where it may be necessary to induce a coma with the use of anesthesia. Artificial comas are generally induced with barbiturates, such as pentobarbital or thiopental, because such drugs reduce the metabolic rate of brain tissue as well as cerebral blood flow which narrows the blood vessels in the brain and reduces pressure and swelling. The theory supporting such treatment is that it helps to prevent further brain damage in cases of injury and to prevent restriction on the neurosurgeon's ability to perform the necessary tasks. During such treatments or situations, brain or cortical activity monitoring is necessary to ensure the health and safety of the patient.

Another step of various embodiments of the present invention includes measuring the brain or cortical activity of both the subject's left and right brain hemispheres essentially simultaneously. In order to measure the brain or cortical activity from the raw EEG signal, that signal must be "pre-processed" in order to get it into a form that is measurable and which can provide the pertinent information. Generally, pre-processing steps include signal amplification, initial hardware filtering methods, artifact detection and removal, analog-to-digital conversion, further software filtering, and the like. Physiological signals generally need to be amplified because the raw signals are typically at very low strength levels that can be difficult to discern. Amplification magnifies the signals so that they are more manageable to the particular equipment. Initial hardware filtering methods are used to try to minimize or eliminate any ambient signal interference (e.g. electromagnetic interference) that can corrupt the desired signal and prevent accurate signal analysis. Additional filtering such as artifact detection processes identify further signal perturbations including, but not limited to other signals such as electromagnetic interference that was not filtered out, and in the case of EEG monitoring, other physiological signals such as EMG, EOG, ECG, and the like. In addition, head or body movements can result in EMG artifacts that need to be removed as well. Accordingly, QEEG indices can be calculated for each of these separate components of the EEG signal and displayed individually or in combination with other QEEG indices. Along with detecting these artifacts it is necessary to try and remove them to leave only the unperturbed, raw signal that is desired, the EEG signal. Digital signal conversion is also required in order to take the raw physiological signal and transform it into an electrical signal that can be measured, analyzed and recorded by the given hardware. Digital signal conversion can take place also before some or all of the filtering. Once the signal has undergone both filtering and conversion from analog to digital it is then ready to undergo the appropriate and necessary analytical and analysis techniques.

Analytical and analysis techniques are needed to measure critical features of the EEG signal that allow quantification or QEEG indexing of the subject's brain or cortical activity, depth of anesthesia or sedation, wakefulness and awareness, anesthetic state and the like. These analytical and analysis techniques can include the use of spectral and higher order spectral analysis, wavelets, auditory or somatosensory evoked potentials, and the like. Analytical techniques can include but are not limited to the use of transforms for analyzing and measuring various features of the signal. Different transforms that may be used are Hilbert transform, short-time Fourier transforms, Wigner distributions, Radon transform, Fast Fourier transform, wavelet transform and the like. The most common technique is the use of spectral and higher order spectral analysis such as Fast Fourier transform. The preferred technique is the use of wavelet transform.

As noted above, the measurement of each brain hemisphere's cortical activity is preferably performed essentially simultaneously. 'Essentially simultaneously' refers to the preference that the processor, or processors, record and measure the EEG signal from the left brain hemisphere at substantially the same time as the EEG signal from the right brain hemisphere is recorded and measured. Preferably, the signals from each hemisphere should be recorded and measured within 10 minutes of each other, more preferably within 5 minutes of each other, even more preferably within 1 minute of each other, still more preferably within 30 seconds of each other, even more preferably within 10 seconds of each other, even still more preferably within 1 second of each other, even still more preferably within 500 milliseconds of each other, more preferably still within 100 millisecond of each other, even still more preferably within 10 milliseconds of each other, and most preferably within 1 millisecond of each other.

Yet another step of various embodiments of the present invention involves calculating, with a processor, the QEEG indices relating to the brain or cortical activity corresponding to both the left and right hemisphere of the subject's brain. When the processor is receiving high quality EEG signals from each of the measurement electrodes on each side of the subject's head as well as the reference electrode, it begins to calculate the QEEG index relating to brain or cortical activity for each brain hemisphere. These QEEG indices are calculated by using the variations of the transforms listed above or like techniques known in the art. As mentioned above, the most general technique is through the use of FFT while the preferred technique is with a wavelet transform.

Spectral and higher order spectral analysis is one technique used to provide an accurate and reliable QEEG index of brain or cortical activity. This technique uses a Fast Fourier transform that quantifies non-linearities and phase relationships intrinsic to any waveform such as an EEG signal. Fast Fourier transform analysis is used to take a raw waveform recorded in the time domain (the particular physiological signal recorded over time) and transform it into the frequency components of that signal or power spectrum at a number of time intervals.

Although Fast Fourier transformed (FFT) signals are useful for determining whether some change, pathological activity, or disturbance occurred during the recording of the physiological signal, time information is not present in the Fast Fourier transformed signal. FFT gives what frequency components exist in the signal.

In one embodiment, also described in U.S. Pat. Nos. 4,907,597; 5,010,891; 5,320,107 and 5,458,117, which are herein incorporated by reference, a variation of FFT is used as follows. A filtered, digitized EEG signal recorded over a given period of time is broken down into smaller subsegments of time. For example, a two minute long signal can be divided into four second long intervals creating a set of 30 time intervals. An FFT analysis is then performed on each interval, and the resulting Fats are then used to produce bispectral complex triple product and bispectral real triple product arrays for that interval. The complex triple product arrays of all intervals are added together, and the real triple product arrays of all intervals are also added together. Each element in the final complex array and final real array is then divided by the number of intervals (30 intervals in the above example) to produce an average complex triple product array and an average real triple product array. The magnitude squared of each element in the complex triple product array is divided by the corresponding element in the real triple product array to form the bicoherence array. The bicoherence array is displayed on a video terminal or plotted, and is used as a figure of merit for the assessment of cerebral electrical function.

Since the bispectral process involves an evaluation of the relational components of the fundamental constituents of any signal without regard to the absolute magnitudes of the signals, the bispectral decomposition of the EEG signal yields a unique quantitative description of cerebral electrical behavior. Deviation from normal electrical activity patterns in the brain (whether due to ischemia or anesthesia) will lead to an alteration in the "fine fingerprint" embedded in the structure of the surface EEG signal. Since bispectral analysis is able to extract a quantitative fingerprint inherent in any signal, it provides a unique quantitative index of the influence of ischemia or anesthetic drugs on electrical properties and function of the brain.

Wavelet analysis, on the other hand, is a method that extracts time and frequency information simultaneously addresses some of the limitations of FFT. For this reason, wavelets are more suitable for the analysis of non-stationary or transitory features, which characterize most signals found in biomedical applications. Wavelet analysis uses wavelets transforms for signal decomposition. Wavelet analysis can be viewed as a generalization of Fourier analysis since it introduces time localization in addition to frequency decomposition of a signal. Instead of Fourier analysis which discards time information, wavelets are capable of capturing signal features such as small-scale transients, breakpoints, discontinuities as well as general trends and self-similarity. These features cannot be measured by classical spectral techniques. In addition, wavelets-classes of wave-like functions with a finite number of oscillations, an effective length of finite duration and no offset component—form a basis for the lossless decomposition of a given signal.

The use of wavelet transform significantly reduces the computational complexity when performing the task of assessing the subject's brain activity or cortical state based on an acquired EEG signal. Neither a large number of reference signals nor an extensive amount of clinical EEG data is needed to produce the QEEG index of brain or cortical activity. The methodology of wavelet analysis may also be used to ascertain the state of the brain and the well being of the CNS beyond ascertaining the effects of anesthetic agents on the brain. It may also be used to discriminate between different sleep stages, to assess alertness/drowsiness levels in subjects performing safety critical activities, to evaluate cognitive states such as postoperative and ICU-related cognitive impairment or Alzheimer-related impairment, to detect pre-ictal patterns in order to predict epileptic seizures, to predict seizure duration such as in Electro Convulsive Therapy, to recognize various pathological states of the CNS such as sleep disorders, depression, addiction, ADHD or other psychiatric disorders, to monitor the changes in the cerebral metabolic rate, to establish the blood characteristic at the cortical level, to obtain pharmacodynamic models of anesthetic and other neurological and psychoactive drugs, or to develop titration and dosing profiles for such drugs.

Wavelet analysis represents a signal as a weighted sum of shifted and scaled versions of the original waveform, without any loss of information. A single wavelet coefficient is obtained by computing the correlation between the scaled and time shifted version of the origin al waveform and the analyzed part of a signal. For efficient analysis, scales and shifts take discrete values based on powers of two (i.e., the dyadic decomposition). Wavelet analysis utilizes a hierarchical signal decomposition, in which a given signal is decomposed by a series of low- and high-pass filters followed by down-sampling at each stage. This analysis is referred to as Discrete Wavelet Transform (DWT). The particular structure of the filters is determined by the particular wavelet family used for data analysis and by the conditions imposed for a perfect reconstruction of the original signal.

The approximation is the output of the low-pass filter, while the detail is the output of the high-pass filter. In a dyadic multiresolution analysis, the decomposition process is iterated such that the approximations are successively decomposed. The original signal can be reconstructed from its details and approximation at each stage (e.g., for a 3-level signal decomposition, a signal S can be written as S=A3+D3+D2+D1). The decomposition may proceed until the individual details consist of a single sample. The nature of the process generates a set of vectors (for instance $a_3$, $d_3$, $d_2$, and $d_1$ in the three level signal decomposition), containing the corresponding coefficients. These vectors are of different lengths, based on powers of two. These coefficients are the projections of the signal onto the original waveform at a given scale. They contain signal information at different frequency bands determined by the filter bank frequency response. DWT leads to an octave band signal decomposition that divides the frequency space into the bands of unequal widths based on powers of two.

The Stationary Wavelet Transform (SWT) is obtained in a similar fashion; however, the down-sampling step is not performed. This leads to redundant signal decomposition with better potential for statistical analysis. The frequency space division is the same as for DWT.

Despite its high efficiency for signal analysis, DWT and SWT decompositions do not provide sufficient flexibility for a narrow frequency bandwidth data analysis. Wavelet packets, as a generalization of standard DWT, alleviate this problem. At each stage, details as well as approximations are further decomposed into low and high frequency signal components. Accordingly, a given signal can be written in a more flexible way than provided by the DWT or SWT decomposition (e.g., at level 3 we have S=A1+AD2+ADD3+DDD3, where DDD3 is the signal component of the narrow high frequency band $ddd_3$). Wavelet packet analysis results in signal decomposition with equal frequency bandwidths at each level of decomposition. This also leads to an equal number of the approximation and details coefficients, a desirable feature for data analysis and information extraction.

In one embodiment, also described in U.S. Pat. No. 7,373,198, which is hereby incorporated by reference, a variation of this wavelet transform method is used for EEG analysis as follows. An observed data set is acquired in real-time from a subject's EEG signal. This data set is compared, substantially in real time, with one or more reference data sets which characterize distinct anesthetic states. The comparison yields a QEEG index of brain or cortical activity. This QEEG index can then be used to assist in distinguishing the various stages of general anesthesia, in distinguishing increasing and decreasing depths of general anesthesia, and in detecting the loss of consciousness during the induction of general anesthesia, thus providing an endpoint for individual titration of intravenous induction agents.

The observed and reference data sets are statistical representations of the wavelet coefficients obtained by applying a wavelet transform onto corresponding observed and reference signals. These coefficients may be obtained through a wavelet transform of the EEG such as standard dyadic discrete wavelet transform (DWT), discrete stationary wavelet transform (SWT), or wavelet packet transform. In this respect, filters yielding coefficients in a frequency band, chosen such that their statistical representation differentiates between anesthetic states, can be used for this type of analysis. The observed and reference data sets are obtained by calculating a statistical representation of the transformation coefficients. The methodology of this invention may also be used for extracting information from other physiological signals, such as Electrocardiogram (ECG), representing measured cardiac activity of a subject in order to evaluate the state of the autonomous nervous system of the subject.

The reference data sets represent distinct anesthetic states taken from the continuum from conscious (i.e., fully awake) to isoelectric EEG (i.e., no more brain activity). They are extracted off-line from a group of subjects or patients. They are then stored for substantially real-time implementation. The transformation selected maximizes the dissimilarity between each of the reference data sets.

The comparison between the observed data set against the reference data sets can be based on the computation of the correlation between these functions. However, a computationally less demanding solution is to quantify the similarity between these functions by computing the L1 (Manhattan), L2 (Euclidean), or any distance metrics. In the preferred embodiment, where two reference data sets are used, the result of this comparison yields two values, each expressing the likelihood of a patient being awake or anesthetized. These two values are further combined into a single value corresponding to a univariate QEEG index of brain or cortical activity.

Another step of various embodiments of the present invention involves transmitting the brain or cortical activity indices from the processor to a monitor. The processor calculates the brain or cortical activity indices substantially in real time as it receives the EEG signal from each electrode attached to the subject, and transmits those indices to a monitor for display. This occurs as an electrical signal from the processor containing the current QEEG index relating to brain or cortical activity for a given brain hemisphere which is sent along video connection wires which are attached to the monitor that displays the resultant visual depiction of the indices.

Alternatively, the signal could be broadcast wirelessly from the processor via WiFi network, or a medical band or Bluetooth RF connection to a monitor equipped to receive such signals. The brain or cortical activity indices can be transmitted from the processor to a monitor via these or any other currently available communication methods for visual displays or any that may become available in the future.

Preferably, when using a radio frequency method the system will transmit data in a frequency range, or band, such that it will not receive interference from other radio frequency signals. Preferably, the system will transmit below a frequency of 2.0 GHz to avoid frequency bands that are highly congested, namely the 2.4 GHz band. Operation within these bands over 2.0 GHz may make interference problematic such as by limiting usable bandwidth. Additionally, if power is constant then operation at lower frequencies allows for greater operational range than at higher frequencies. Conversely, operation at lower frequencies consumes less power than higher frequencies over the same range.

Another step of various embodiments of the present invention involves displaying both of the indices on a monitor simultaneously. As the processor is essentially continuously calculating the brain or cortical activity indices for each of the subject's brain hemispheres, it also essentially continuously transmits both indices as described above to a monitor. The monitor(s) receives said signal from the processor and displays the indices corresponding to each of the subject's brain hemispheres adjacent to each other. The QEEG index displays can be oriented vertically (one QEEG index above the other) or horizontally (the two indices side by side). Preferably, each QEEG index is labeled with the corresponding hemisphere (i.e. left or right) which it represents. This label can be provided in text, by the orientation of the QEEG index displays, or by color coding. Even more preferably, the QEEG index display is color coded to match the color of the electrode leads attached to the corresponding side of the subject's head. For example, if the QEEG index display for the left hemisphere is yellow, and the QEEG index display for the right hemisphere is orange, then the electrode leads attached to the left side of the subject's head would be yellow and those attached to the right side would be orange.

Additional display options include but are not limited to displaying the two indices along with: the raw EEG signals as they are acquired, a spectral density graph of the EEG waveform, a display of the signal quality of the electrodes or other sensors, a message or instructions for the caregiver to give the subject attention or perform a task for monitoring, a trend screen showing the history of the brain or cortical activity indices, waveforms for other signals obtained (i.e. EMC, EOG, and the like), any combination of these or other available displays and/or the like.

Yet another step of various embodiments of the present invention includes comparing the indices of each hemisphere's brain or cortical activity. As the processor measures the EEG activity of each of the subject's brain hemispheres and calculates the corresponding brain or cortical activity indices, it also performs a comparison of those two indices substantially in real time. The system notifies the caregiver that there is a potential problem (i.e. signal quality has decreased, subject is showing signs of arousal in one brain hemisphere, subject is experiencing some neuropathological activity, and the like) preferably when the difference between the indices for the left and right hemispheres is greater than 5%, more preferably when the difference is greater than 10%, even more preferably when the difference is greater than 12%, still more preferably when the difference is greater than 15% and most preferably when the difference is greater than 20%. Small differences in the indices less than 5% are usually common in normal functioning brain activity, and notification of differences in that range would present an increase in false diagnosis of problems.

Another step of various embodiments of the present invention includes determining whether the signal of at least one of the EEG electrodes is likely to have too high of impedance. One object of the present invention is to use the calculated brain or cortical activity indices from each of the subject's brain hemispheres, more particularly the difference between those indices, to determine whether a problem or condition exists in measurement or with the subject or patient. If the calculated indices are too dissimilar, then the system determines there may be a problem, which may be either poor signal quality or may be a physiological condition or problem with the subject or patient. To test for poor signal quality, an electrical impulse is provided to the sensor or electrode and the system measures the resulting electrical impedance of that sensor or electrode. This can be done automatedly when the difference between indices is too high, or the system may provide a message to a caregiver to manually instruct the system to perform the test. If the measured electrical impedance is high, the caregiver can improve signal quality by replacing the sensor or electrode, applying conductive gel and reseating the sensor or electrode, re-abrading the subject's skin and reapplying the sensor or electrode, or any other available means to address the issue. Electrical impedance can be as high as 5 to 10 K ohms in typical electrode connections, but for good signal quality, impedance is preferably maintained less than 5 K ohms, more preferably less than 4 K ohms, even more preferably less than three K ohms, and most preferably at 2 K ohms or less.

Another step of various embodiments of the present invention includes determining whether the brain or cortical activity of one hemisphere of the brain is indicative of a neuropathological condition when compared to the brain or cortical activity of the other hemisphere of the brain of the subject. One object of the present invention is to use the calculated brain or cortical activity indices from each of the subject's brain hemispheres, more particularly the difference between those indices, to determine whether the subject is experiencing some form of neuropathological activity (i.e. stroke, seizure, and the like). If the calculated indices are too dissimilar, then the system determines there may be a problem, which may be such neuropathological activity (e.g., include but are not limited to stroke, regional perfusion disturbances, ischemia, metabolic dysfunction, regional seizure, hypotension and hypertension related disturbances, and the like). Once determining that a potential neuropathological activity or disturbance is occurring or has occurred, the system notifies a physician, clinician, or other caregiver that such a problem is or has occurred so that person can administer the proper treatment to the subject or patient.

Similar to above, asymmetry thresholds in the brain or cortical activity indices for each brain hemisphere may be indicative of potential neuropathological activity, and this will indicate as such when the difference between the indices for the left and right hemispheres is greater than 5%, more preferably when the difference is greater than 10%, even more preferably when the difference is greater than 12%, still more preferably when the difference is greater than 15% and most preferably when the difference is greater than 20%. Small differences in the indices less than 5% are usually common in normal functioning brain activity, and notification of differences in that range would present an increase in false diagnosis of problems.

The calculated indices are not used to diagnose the specific type of neuropathological activity which is or has occurred. EEG signals, and specifically QEEG, generally only indicate that a problem exists, or rather than some abnormal activity has occurred. The caregiver who reads and interprets these signals has the responsibility to coordinate all of the factors surrounding the subject or patient and make a determination of what the most likely cause of the neuropathological activity is.

Another step of various embodiments of the present invention involves determining whether the brain or cortical activity of one hemisphere of the brain is indicative of a change in subject status when compared to the brain or cortical activity of the other hemisphere of the brain of the subject. One object of the present invention is to use the calculated brain or cortical activity indices from each of the subject's brain hemispheres, more particularly the difference between those indices, to determine whether the subject is showing signs of muscle activity as a reaction to some pain or other stimulus, in one hemisphere that is not shown in the other. If the calculated indices are too dissimilar, then the system determines there may be a problem, which is may indicate that the subject's brain is reacting to some condition, event, or occurrence. If one hemisphere of the subject's brain experiences and reacts to pain or noxious stimuli or discomfort and produces involuntary reactions, the caregiver(s) may assume that additional sedative or anesthetic medication is necessary. However, if the other hemisphere is still fully anesthetized or sedated when the additional medication is administered, that hemisphere can be monitored for overdosing. Another possibility when the indices are too dissimilar is that some neuropathological activity may be occurring in one hemisphere, such as stroke, seizure, and the like.

When a subject requires additional sedative or anesthetic medication, the above dosing issues need to be addressed prior to administering said medication. One option is to determine whether medication is needed, and the dose required, based on the brain hemisphere that has the higher calculated QEEG index corresponding to a higher level of alertness, wakefulness or awareness. This method prevents one of the subject's brain hemispheres from becoming alert or wakeful enough to become cognitive of pain or other surrounding circumstances. However, this leads to the potential of overdosing the brain hemisphere of the subject's brain that is still adequately sedated or anesthetized. Another option, is to determine whether medication is needed, as well as the dose required, based on the brain hemisphere that has a lower calculated QEEG index corresponding to deeper sedation or anesthesia. This method decreases the risk of overdosing either hemisphere of the subject's brain; however, it increases the risk that one of the subject's brain hemispheres will become more alert and possibly rise to the level of cognition of pain or other surrounding circumstances. This method also potentially allows for lower overall dosing of anesthesia drugs and sedatives.

Other possible options are hybrid, least risk dosing techniques. One least risk approach is to verify that the two indices are similar, and if they are not, the closed-loop system should warn the user and stop adjusting the drug automatically allowing the notified user to monitor the subject and perform the adjustments as necessary. In this case, the bilateral feature is used for redundancy. Another least risk approach is to have the anesthesiologist choose the index used to titrate the drug if the two indices are significantly different. Another approach is to automatically make this determination based on agreed-upon rules (for example, use the index for which the signal quality is better, or always use the minimum of the two indices, or always use the maximum of the two indices, or use the average of the two, or use some other linear or nonlinear combination of the two indices depending on the anesthesia delivery goals and needs). Yet another option would be to select a lower limit and an upper limit such that both indices are kept between these two limits. Yet another option would be to select a lower limit such that at least one of the indices is kept above this limit. Yet another option would be to select an upper limit such that at least one of the indices is kept below this limit. Other combinations of the lower and upper limits and indices behaviors in relation hip to these limits cam be envisioned based on anesthesia delivery goals and needs, and are intended to be included within the scope of the present invention. In utilizing this method, preferably the upper limit corresponds to 50% probability of a subject being awake, more preferably to 60% probability of a subject being awake, even more preferably to 70% probability of a subject being awake, more preferably still to 80% probability of a subject being awake, yet more preferably to 90% probability of a subject being awake, and even more preferably to 95% probability of a subject being awake. Further, in utilizing this method, preferably the lower limit corresponds to 5% suppression of a subject's brain or cortical activity, more preferably to 10% suppression of a subject's brain or cortical activity, even more preferably to 20% suppression of a subject's brain or cortical activity, still more preferably to 30% suppression of a subject's brain or cortical activity, and even more preferably to 35% suppression of a subject's brain or cortical activity. Further, in utilizing this method, the lower and upper limits can be chosen to correspond to different probabilities of various clinical endpoints, such as probability of patient movement, probability of patient forming memory recall, probability of patient reaction or response, probability of patient being hypo- or hyper-tensive, and the like. Many different combinations of the lower and upper limits and clinical endpoints can be envisioned based on anesthesia delivery goals and needs, and are intended to be included within the scope of the present invention.

Another step of various embodiments of the present invention includes displaying a message, either audible or visual, or a combination thereof, notifying a caregiver that some attention is needed by the patient and/or brain or cortical activity quantification device. It is not always immediately apparent simply by looking at the monitor or the indices displayed for the brain or cortical activity of each of a subject's brain hemispheres when there is a potential problem with the equipment or the subject. Furthermore, there are certain circumstances (e.g. long term EEG monitoring and care, sleep studies, and the like) where no caregiver may be actively attending to the subject and monitor on a full-time basis and may not see when the indices indicate a potential problem. For these reasons, the present invention preferably includes the ability to display a message or notify a caregiver in some way to tend to the subject. Several types of messages or signals are discussed below, and can be used individually or in any type of combination with each other, This list is by no means exhaustive.

One option for notifying the caregiver is to display a message on the monitor where the brain or cortical activity indices are displayed. This message may be a textual one that scrolls across the screen, flashes on the screen, appears and blinks, and the like. Furthermore, the caregiver may be alerted by color (e.g., red) to distinguish the message from the rest of the monitoring information on the screen. The text itself may appear in color or may appear in a colored frame or box.

Another option for notifying a caregiver is to display a message on the monitor in the form of a symbol, rather than actual text. Basic shapes can be used to indicate different potential issues that may arise. These symbols may scroll across the screen, flash on the screen, appear on the screen and blink, and the like. The symbols may also be displayed in color to distinguish the symbol from the rest of the monitoring information on the screen. A symbol can also be used in combination with text as well.

Yet another option for notifying a caregiver is to sound an audible signal or message to get the attention of a caregiver. The audible signal can be a tonal sounding, such as a single beep, multiple beeps, or a longer tone. The message could be synthesized speech or a prerecorded message. Furthermore, different combinations of beeps can be used to indicate different possible issues. Any combination of audible and visual signals and/or messages may also be used. Still another option for notifying a caregiver is to send a message to a pager, computer, PDA (personal digital assistant), cell phone, or phone in case said caregiver is not in the immediate vicinity of the subject.

Now referring to the FIGS. 1-11, FIG. 1 is a flow chart describing a process for monitoring and measuring electrode signal quality using the bilateral monitoring techniques described herein. A subject is attached to the bilateral monitoring system with an electrode array that measures signals from both hemispheres of the subject's brain (not shown). Preferably, the electrode array involves the placement of electrodes on the subject's head in such a manner that the measurement electrodes are substantially equidistant from the center of the subject's head which corresponds to the longitudinal fissure of the brain separating the two brain hemispheres along the sagittal plane of the subject's body. Also preferably, at least two measurement electrodes are placed substantially symmetrically as described, at least one measurement electrode being placed on each side of the subject's head to measure the brain or cortical activity of each brain hemisphere. A reference electrode is placed in the center of the subject's head, substantially near the location of the longitudinal fissure (not shown). Once the electrode array is in place, the subject's brain or cortical activity in each brain hemisphere is monitored at substantially the same time 1.

After monitoring the subject's brain or cortical activity for each hemisphere, the subject is anesthetized or sedated 3, and when the subject is fully anesthetized or sedated, the brain or cortical activity in each of the subject's brain hemispheres is then measured individually but at substantially the same time 5 and preferably on a continuous basis. The measurements are performed on each hemisphere via the measurement electrode on for the given hemisphere and the common reference electrode along the longitudinal fissure (not shown). As the EEG signal is monitored and measured from each brain hemisphere, the system calculates individual brain or cortical activity indices 7 for each of the subject's brain hemispheres that quantifies the subject's brain or cortical activity, corresponds to the level of wakefulness or awareness, or conversely the level of sedation, that each of the subject's brain hemispheres are experiencing. These brain or cortical activity indices range between the values of zero (indicating brain death) and 100 (indicating complete wakefulness and awareness)—however other types of indices may be used as well. As these indices are calculated for each brain hemisphere, they are displayed substantially in real time and substantially at the same time on a monitor 9 for the caregiver to see and use to evaluate the needs of the subject. Optionally, the method can include a warning or message (not shown) to the caregiver indicating a significant difference between the two indices. This warning or message can be a flashing light, a message on the monitor, a bell, or the like.

If the signal quality decreases or becomes compromised, the caregiver, if properly trained should notice the differences in the indices on the screen and check the electrodes to determine if a problem exists 11. While significant differences in the indices could be indicative of signal quality—this could also reflect other physiological conditions of the subject as well. There are several common issues that cause a decrease in signal quality, including, but not limited to, conductive gel between the electrode and subject's skin becoming dry 13, the electrode itself being bad or failing 17, or the electrode having moved from its original position 21. If the caregiver finds that differences in the indices are indicative of high impedances in one or more of the electrodes then the caregiver should check the electrode(s) to see what possible issue or problem has caused the poor signal quality and makes the necessary adjustments to repair the connection and restore good signal quality. If the caregiver notices that the conductive gel has dried up 13 (only an issue with electrodes that require such gel, not with dry electrodes), then the caregiver simply reapplies conductive gel to the surface of the electrode or the subject's skin and reapplies the electrode to the subject 15. If it is determined that the electrode itself is bad 17 and unable to accurately conduct a signal at all, then the caregiver discards the bad electrode and replaces it with a new one 19 in the same manner and position as the first one was applied. If the electrode has moved from the position in which it was initially placed 21, the caregiver can then reseat the electrode or may need to re-abrade the subject's skin 23 under the electrode before reseating the electrode into position in order to retrieve a sufficient signal. Once the problem has been appropriately addressed, and all of the electrodes are accurately and sufficiently conducting an EEG signal from the subject to the system and monitor, the caregiver can then reinitializes 25 or starts the signal acquisition and subsequent monitoring and measurement of brain or cortical activity in each of the subject's brain hemispheres.

Figure 2:
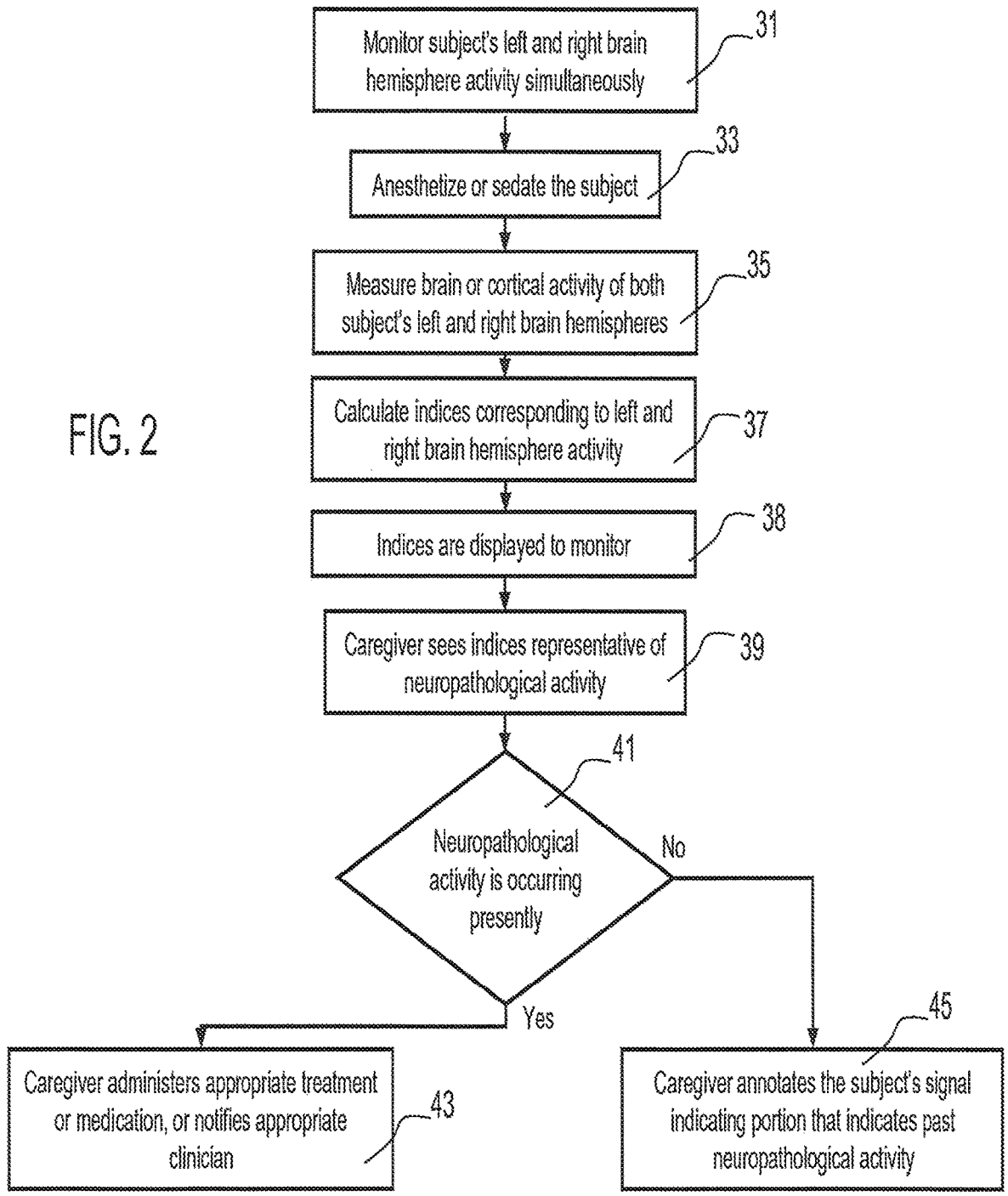
FIG. 2. Flowchart depicting a process of detecting past or present neuropathological activity in the subject's brain.

FIG. 2 is a flowchart depicting the process of detecting the presence of past or present neuropathological activity in one of the subject's brain hemispheres using the bilateral monitoring system. A subject is attached to the bilateral monitoring system with an electrode array that measures signals from both hemispheres of the subject's brain (not shown). Preferably, the electrode army involves the placement of electrodes on the subject's head in such a manner that the measurement electrodes are substantially equidistant from the center of the subject's head which corresponds to the longitudinal fissure of the brain separating the two brain hemispheres along the sagittal plane of the subject's body. Also preferably, at least two measurement electrodes are placed substantially symmetrically as described, at least one measurement electrode being placed on each side of the subject's head to measure the brain or cortical activity of each brain hemisphere. A reference electrode is placed in the center of the subject's head, substantially near the location of the longitudinal fissure (not shown). Once the electrode array is in place, the subject's brain or cortical activity in each brain hemisphere is monitored at substantially the same time 31.

After monitoring the subject's brain or cortical activity for each hemisphere, the subject is anesthetized or sedated 33, and when the subject is fully anesthetized or sedated, the brain or cortical activity in each of the subject's brain hemispheres is then measured individually but at substantially the same time 35 and preferably on a continuous basis. The measurements are performed on each hemisphere via the measurement electrode on for the given hemisphere and the common reference electrode along the longitudinal fissure (not shown). As the EEG signal is monitored and measured from each brain hemisphere, the system calculates individual brain or cortical activity indices 37 for each of the subject's brain hemispheres that quantifies the subject's brain or cortical activity, corresponds to the level of wakefulness or awareness, or conversely the level of sedation, that each of the subject's brain hemispheres are experiencing. These brain or cortical activity indices range between the values of zero (indicating brain death) and 100 (indicating complete wakefulness and awareness)—however other types of indices may be used as well. As these indices are calculated for each brain hemisphere, they are displayed substantially in real time and substantially at the same time on a monitor 38 for the caregiver to see and use to evaluate the needs of the subject. Optionally, the method can include a warning or message (not shown) to the caregiver indicating a significant difference between the two indices. This warning or message can be a flashing light, a message on the monitor, a bell, or the like.

If the caregiver notices that the brain or cortical activity indices displayed on the monitor are substantially different and/or indicative of some neuropathological activity 39 such as seizure, stroke, or some other neurological problem, then the caregiver initially determines whether the neuropathological activity is occurring contemporaneously, or at the present time 41. If the neuropathological activity is occurring at that time, then the caregiver immediately notifies the appropriate clinician or administers the necessary treatment or medication 43 to handle the activity and minimize damage to the subject. If the subject is not presently experiencing the indicated neuropathological activity, but rather had suffered it in the past, then the clinician annotates the portion of the subject's EEG signal 45 from the hemisphere that shows the past activity for future reference and/or treatment.

Figure 3:
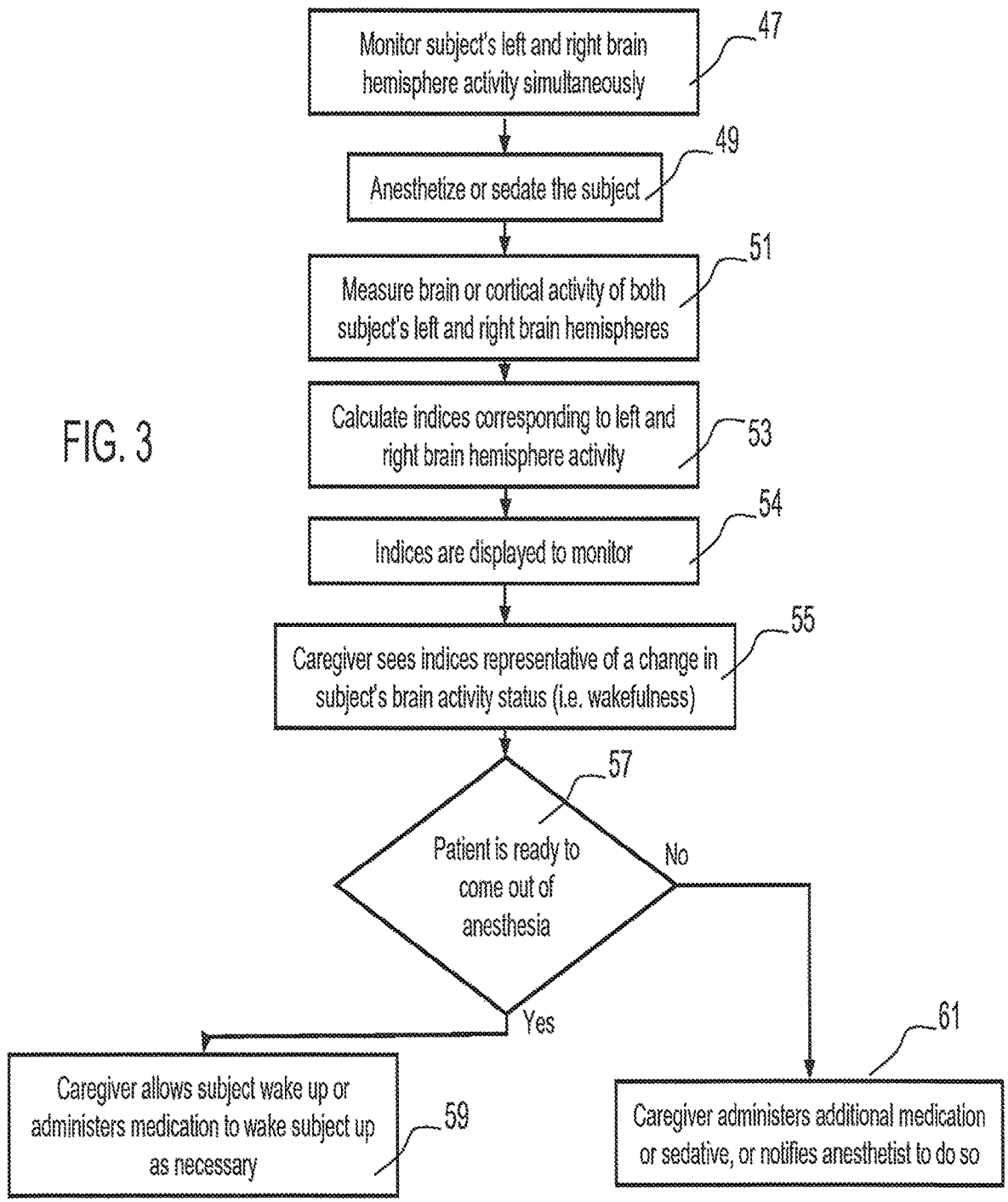
FIG. 3. Flowchart depicting a process of detecting changes in the subject's brain or cortical activity.

FIG. 3 is a flowchart showing the process of monitoring a subject's status with regard to cortical or brain activity as a measure of wakefulness or awareness or reaction to noxious or surgical stimulation using the bilateral monitoring system and method. A subject is attached to the bilateral monitoring system with an electrode array that measures signals from both hemispheres of the subject's brain (not shown). Preferably, the electrode array involves the placement of electrodes on the subject's head in such a manner that the measurement electrodes are substantially equidistant from the center of the subject's head which corresponds to the longitudinal fissure of the brain separating the two brain hemispheres along the sagittal plane of the subject's body. Also preferably, at least two measurement electrodes are placed substantially symmetrically as described, at least one measurement electrode being placed on each side of the subject's head to measure the brain or cortical activity of each brain hemisphere. A reference electrode is placed in the center of the subject's head, substantially near the location of the longitudinal fissure (not shown). Once the electrode array is in place, the subject's brain or cortical activity in each brain hemisphere is monitored at substantially the same time 47.

After monitoring the subject's brain or cortical activity for each hemisphere, the subject is anesthetized or sedated 49, and when the subject is fully anesthetized or sedated, the brain or cortical activity in each of the subject's brain hemispheres is then measured individually but at substantially the same time 51 and preferably on a continuous basis. The measurements are performed on each hemisphere via the measurement electrode on for the given hemisphere and the common reference electrode along the longitudinal fissure (not shown). As the EEG signal is monitored and measured from each brain hemisphere, the system calculates individual brain or cortical activity indices 53 for each of the subject's brain hemispheres that quantifies the subject's brain or cortical activity, corresponds to the level of wakefulness or awareness, or conversely the level of sedation, that each of the subject's brain hemispheres are experiencing. These brain or cortical activity indices range between the values of zero (indicating brain death) and 100 (indicating complete wakefulness and awareness)—however other types of indices may be used as well. As these indices are calculated for each brain hemisphere, they are displayed substantially in real time and substantially at the same time on a monitor 54 for the caregiver to see and use to evaluate the needs of the subject. Optionally, the method can include a warning or message (not shown) to the caregiver indicating a significant difference between the two indices. This warning or message can be a flashing light, a message on the monitor, a bell, or the like.

If the indices displayed are substantially different for each of the subject's brain hemispheres or they indices begin to change, or in some other way indicate that there is a change in the subject's brain or cortical state or brain activity, the caregiver notices this change in the displayed indices 55. When this occurs, the caregiver must determine where in the treatment process the subject is 57. If the subject is done with the given treatment, process or procedure for which it was sedated or anesthetized, then the caregiver can either allow the subject to naturally come out of the sedated or anesthetized state or can administer medication 59 to return subject to alert state more quickly. If the indices show that the subject is becoming alert, or that one brain hemisphere is more alert than the other (though the total effect is that the subject appears fully sedated or anesthetized) and it is not the appropriate time for the subject to come out of sedation or anesthesia, then the caregiver can adjust the level of medication or administer additional medication as necessary to increase the level of sedation and return the hemisphere(s) back to a state of no alertness, wakefulness or awareness.

Figure 4:
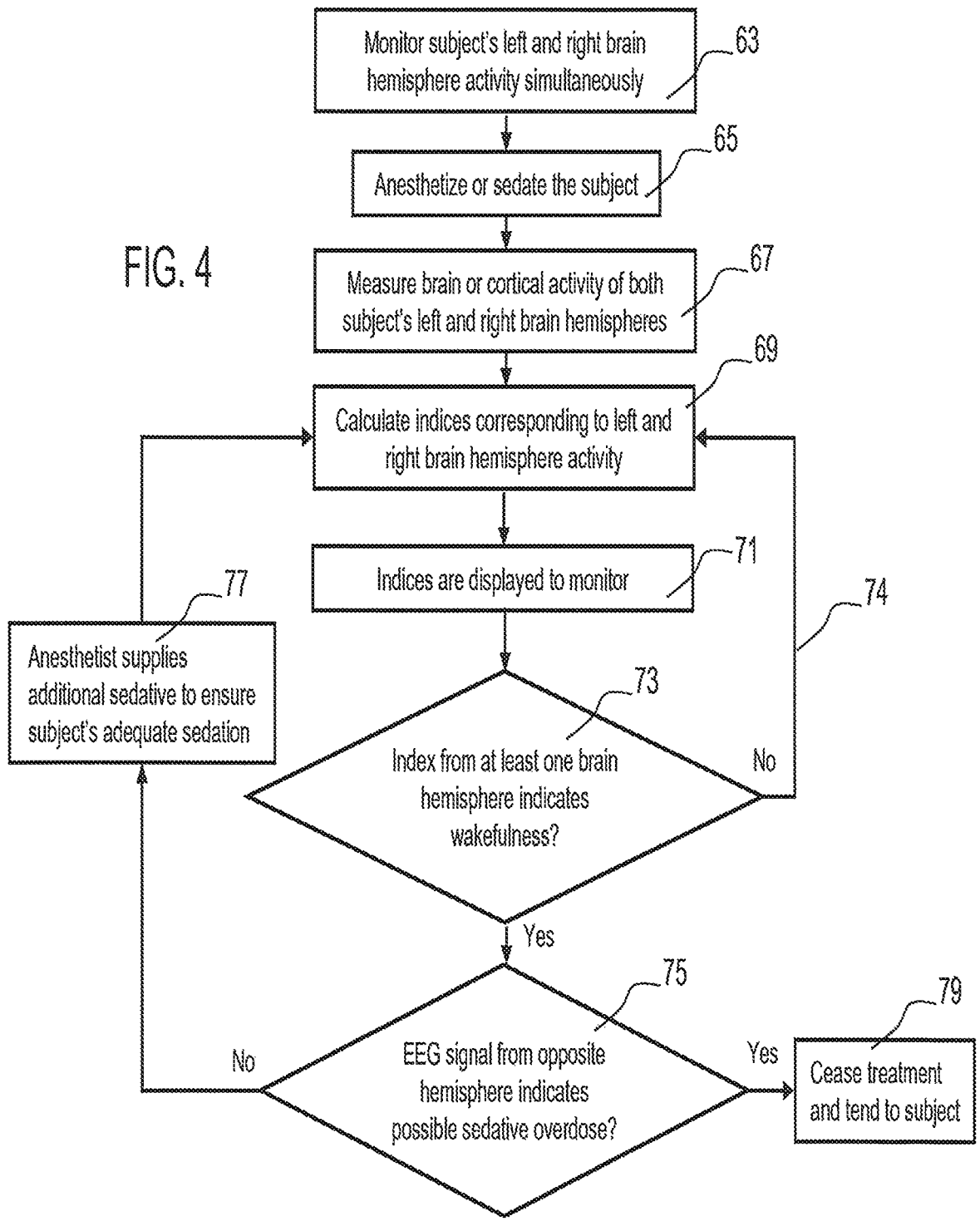
FIG. 4. Flowchart depicting a closed-loop medication delivery system for maintaining sedation or anesthetization of a subject.

FIG. 4 is a flow chart showing a process of closed-loop delivery of medication utilizing a least-risk approach to minimize the level of medication needed to sedate or anesthetize a subject while maintaining a sufficient level of sedation or anesthesia ensuring the patient is not alert or awake during the procedure, treatment or process. A subject is attached to the bilateral monitoring system with an electrode array that measures signals from both hemispheres of the subject's brain (not shown). Preferably, the electrode array involves the placement of electrodes on the subject's head in such a manner that the measurement electrodes are substantially equidistant from the center of the subject's head which corresponds to the longitudinal fissure of the brain separating the two brain hemispheres along the sagittal plane of the subject's body. Also preferably, at least two measurement electrodes are placed substantially symmetrically as described, at least one measurement electrode being placed on each side of the subject's head to measure the brain or cortical activity of each brain hemisphere. A reference electrode is placed in the center of the subject's head, substantially near the location of the longitudinal fissure (not shown). Once the electrode array is in place, the subject's brain or cortical activity in each brain hemisphere is monitored at substantially the same time 63.

After monitoring the subject's brain or cortical activity for each hemisphere, the subject is anesthetized or sedated 65, and when the subject is fully anesthetized or sedated, the brain or cortical activity in each of the subject's brain hemispheres is then measured individually but at substantially the same time 67 and preferably on a continuous basis. The measurements are performed on each hemisphere via the measurement electrode on for the given hemisphere and the common reference electrode along the longitudinal fissure (not shown). As the EEG signal is monitored and measured from each brain hemisphere, the system calculates individual brain or cortical activity indices 69 for each of the subject's brain hemispheres that quantifies the subject's brain or cortical activity, corresponds to the level of wakefulness or awareness, or conversely the level of sedation, that each of the subject's brain hemispheres are experiencing. These brain or cortical activity indices range between the values of zero (indicating brain death) and 100 (indicating complete wakefulness and awareness)—however other types of indices may be used as well. As these indices are calculated for each brain hemisphere, they are displayed substantially in real time and substantially at the same time on a monitor 71 for the caregiver to see and use to evaluate the needs of the subject. Optionally, the method can include a warning or message (not shown) to the caregiver indicating a significant difference between the two indices. This warning or message can be a flashing light, a message on the monitor, a bell, or the like.

Rather than a caregiver continuously monitoring the brain or cortical activity indices for changes in subject status, brain or cortical activity, or neuropathological activity, predetermined thresholds are used for closed-loop medication delivery to indicate to the system when the subject shows signs of such changes or conditions in the subject. The system initially uses the brain or cortical activity indices calculated for each of the subject's brain hemispheres to determine whether either one or both of the hemispheres shows signs of wakefulness or alertness 73 which indicates the subject's brain is coming out of sedation or anesthesia in the corresponding hemisphere. As long as neither QEEG index shows signs of wakefulness or awareness in either of the subject's brain hemispheres, the system continues to monitor and measure the individual hemispheres' EEG signals and calculate the corresponding indices 74. However, if at least one of the brain or cortical activity indices indicates that the corresponding brain hemisphere is becoming alert or waking, then the system next attempts to determine the level of anesthesia or sedation medication that has already been administered to determine whether the subject is close to overdose of said medication 75.

The determination of overdose, or near overdose, of medication is made as a function of the difference between brain or cortical activity indices in each of the subject's brain hemispheres. If the QEEG index of one hemisphere indicates that it is becoming alert, and the QEEG index of the other shows similar signs, then it is likely safe for an anesthetist or appropriate caregiver to administer additional sedative or anesthesia medication 77 to return the subject to sufficient levels of sedation or anesthesia. However, if the QEEG index relating to brain or cortical activity of one brain hemisphere shows signs of becoming alert and the other shows signs of continued deep sedation or anesthesia, then it is not safe to administer additional medication or the subject would run the risk of overdosing. In such event, the caregivers must cease treatment and tend to the subject as necessary 79 in order to prevent harm to the subject either through lack of sedation or overdose thereof.

Figure 5:
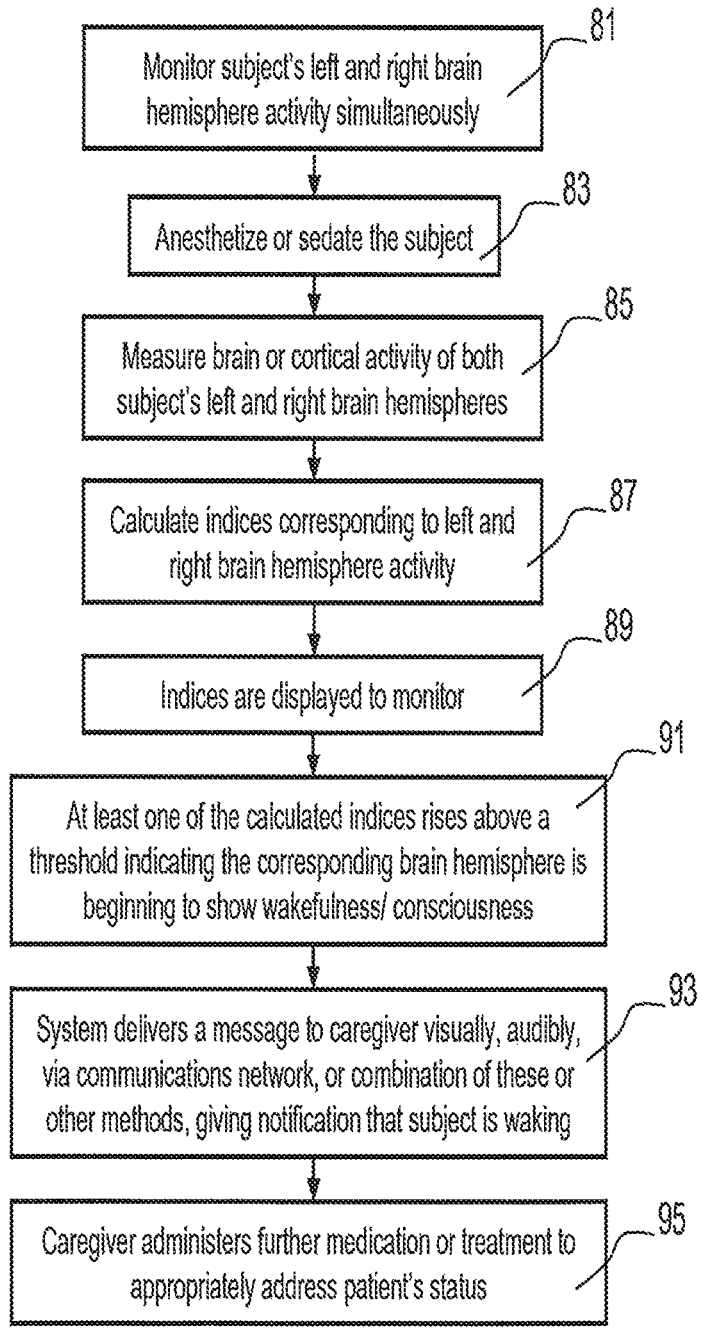
FIG. 5. Flowchart depicting a process of delivering a message to a caregiver based on the calculated brain or cortical activity indices that a subject requires attention.

FIG. 5. is a flow chart depicting a process of delivering a message to a caregiver utilizing the bilateral monitoring system and method by which the caregiver is notified of any type of significant change or occurrence in the subject's status, brain or cortical activity, or condition. A subject is attached to the bilateral monitoring system with an electrode array that measures signals from both hemispheres of the subject's brain (not shown). Preferably, the electrode array involves the placement of electrodes on the subject's head in such a manner that the measurement electrodes are substantially equidistant from the center of the subject's head which corresponds to the longitudinal fissure of the brain separating the two brain hemispheres along the sagittal plane of the subject's body. Also preferably, at least two measurement electrodes are placed substantially symmetrically as described, at least one measurement electrode being placed on each side of the subject's head to measure the brain or cortical activity of each brain hemisphere. A reference electrode is placed in the center of the subject's head, substantially near the location of the longitudinal fissure (not shown). Once the electrode array is in place, the subject's brain or cortical activity in each brain hemisphere is monitored at substantially the same time 81.

After monitoring the subject's brain or cortical activity for each hemisphere, the subject is anesthetized or sedated 83, and when the subject is fully anesthetized or sedated, the brain or cortical activity in each of the subject's brain hemispheres is then measured individually but at substantially the same time 85 and preferably on a continuous basis. The measurements are performed on each hemisphere via the measurement electrode on for the given hemisphere and the common reference electrode along the longitudinal fissure (not shown). As the EEG signal is monitored and measured from each brain hemisphere, the system calculates individual brain or cortical activity indices 87 for each of the subject's brain hemispheres that quantifies the subject's brain or cortical activity, corresponds to the level of wakefulness or awareness, or conversely the level of sedation, that each of the subject's brain hemispheres are experiencing. These brain or cortical activity indices range between the values of zero (indicating brain death) and 100 (indicating complete wakefulness and awareness)—however other types of indices may be used as well. As these indices are calculated for each brain hemisphere, they are displayed substantially in real time and substantially at the same time on a monitor 89 for the caregiver to see and use to evaluate the needs of the subject. Optionally, the method can include a warning or message (not shown) to the caregiver indicating a significant difference between the two indices. This warning or message can be a flashing light, a message on the monitor, a bell, or the like.

As the brain or cortical activity QEEG index of one or both of the subject's brain hemispheres rises corresponding to a change in the subject's status, condition, or the occurrence of some neuropathological activity, the system monitors the rise. If at least one of the QEEG indices reaches a predetermined threshold value, the system determines that the corresponding hemisphere is experiencing a change 91, such as becoming alert or wakeful or experiencing neuropathological activity. When the system makes this determination it then delivers a message to a caregiver 93 who can address the change in the subject accordingly. This message can be delivered in numerous ways: visual display on the monitor, audible notification such as a beep indicating attention is necessary, or through telecommunications networks such as sending a page or text message to the appropriate caregiver's pager or phone. Upon receiving the message from the system that a change has occurred and the subject needs some form of attention, the caregiver can go to the subject and administer the appropriate care or attention 95.

Figure 6:
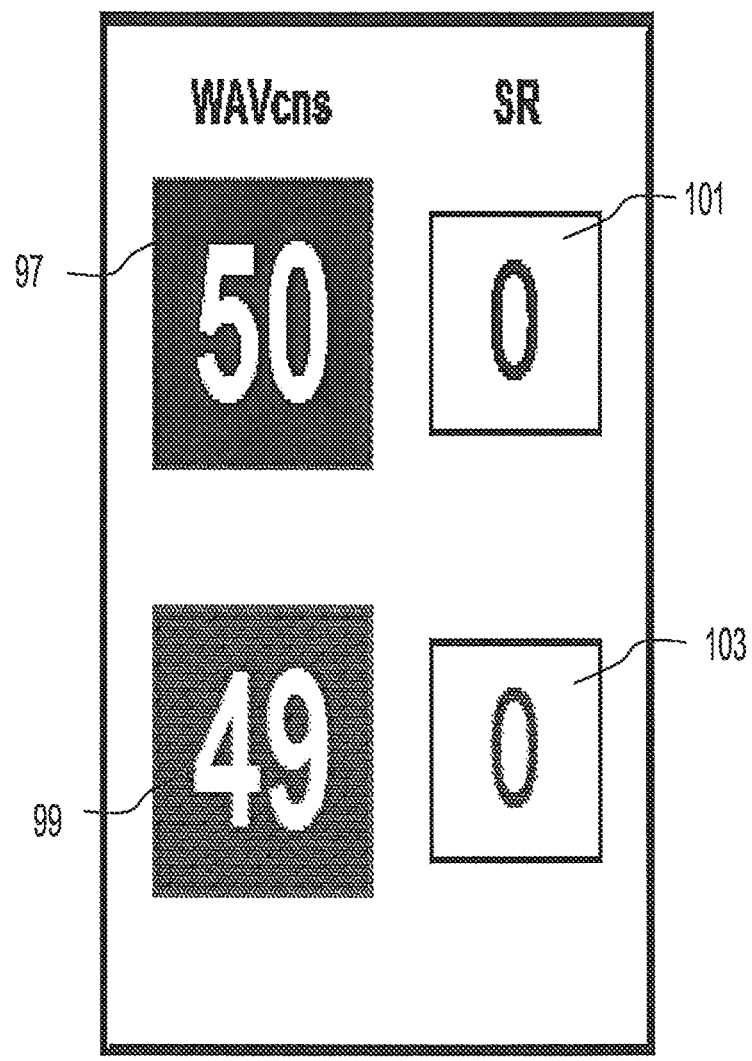
FIG. 6. Image showing a representation of two brain or cortical activity indices calculated for each of a subject's brain hemispheres.

FIG. 6 is a schematic of one embodiment of a display of two indices calculated corresponding to the brain or cortical activity of a subject's brain hemispheres. The display 96 in this embodiment is used to show the right 97 and left 99 brain hemispheres' brain or cortical activity or level of consciousness. The brain or cortical activity QEEG index is calculated by one or more of the steps listed above. The QEEG index for the right brain hemisphere, in this example, is surrounded by colored box 98 (shown as shading), the color which is coordinated with an orange electrode lead (not shown) attached to the right ride of the subject's head (not shown). Similarly, the brain or cortical activity QEEG index is calculated and displayed for the left brain hemisphere 99. The QEEG index for the left brain hemisphere, in this example, is surrounded by a yellow box 100 (shown as a different level of shading) which is coordinated with a yellow electrode lead (not shown) attached to the left ride of the subject's head (not shown). Additional information such as the suppression ratio (left hemisphere) 101 and suppression ratio (right hemisphere) 103 for each brain hemisphere, which represents the amount of time with no substantial brain or cortical activity, may also be incorporated into the display 96. Optionally, the QEEG indices can display just the index numbers 97 and 98 where the actual number, rather than the surrounding box is color coded.

Figure 7:
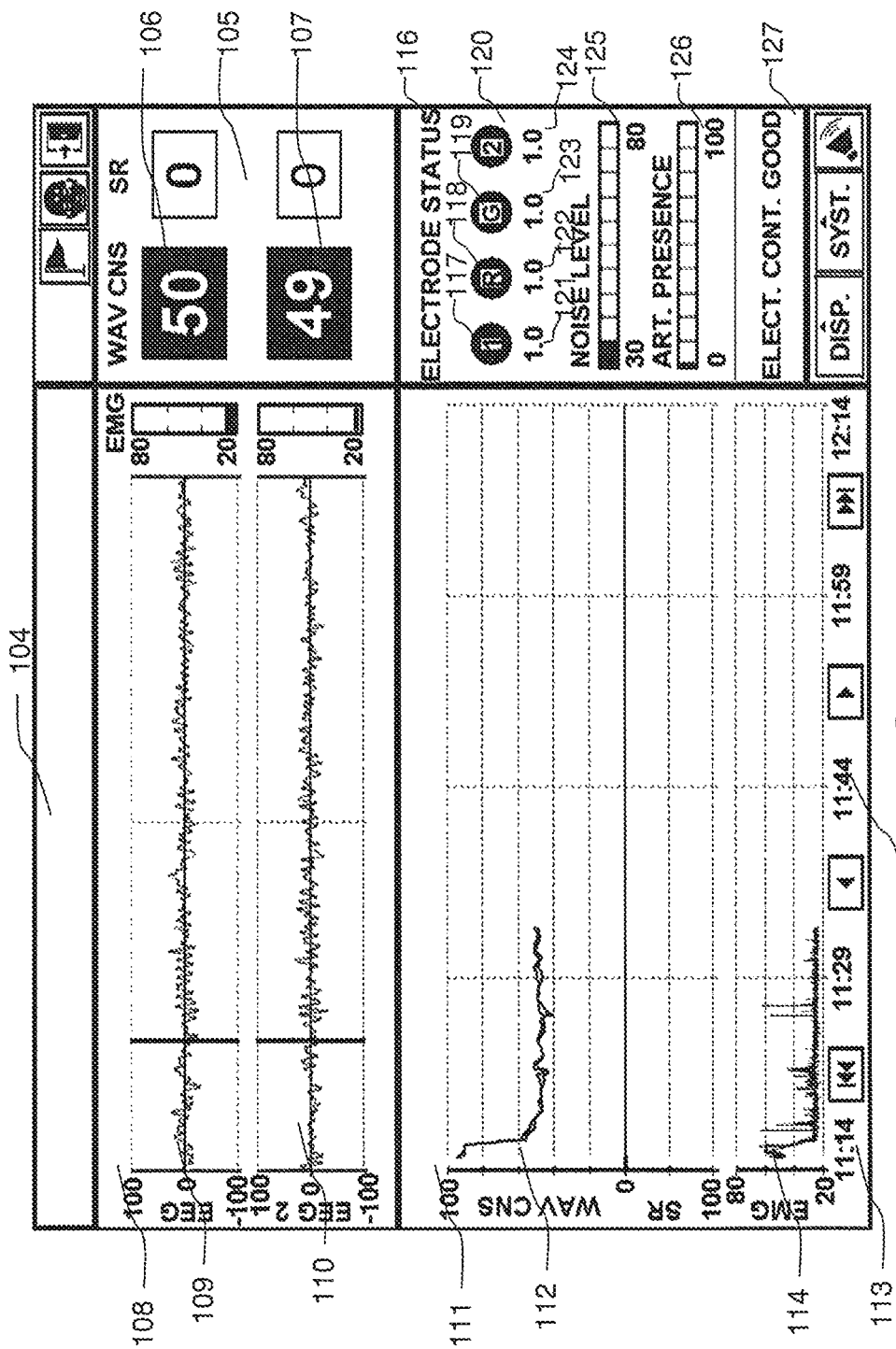
FIG. 7. Image demonstrating brain or cortical activity indices for each of a subject's brain hemispheres along with corresponding EEG waveforms from each hemisphere, other physiological signals being collected (e.g. EMG), as well as the status of the electrode signal quality.

FIG. 7 is a schematic of another embodiment of a display showing the two calculated indices and additional information related to the subject being monitored. In this display 104, the individual brain or cortical activity indices 106 & 107 for each brain hemisphere are shown in the upper right portion 105 of the display 104 displayed in color (not shown) corresponding, as described above, preferably to the electrode lead used (not shown).

The individual raw EEG waveforms 109 & 110 for each brain hemisphere are displayed in the upper left portion 108 of the display 104. The waveforms preferably are displayed in color (not shown) matching the color of the corresponding QEEG index 106 & 107 as well as the corresponding electrode (not shown) lead acquiring the given signal. In this embodiment, the right brain hemisphere EEG waveform 109 and QEEG index 106 are displayed in orange while the left hemisphere EEG waveform 110 and QEEG index 107 are displayed in yellow. If a spike is recorded in one of the hemisphere EEG waveforms displayed indicating that some brain or cortical activity has occurred, the corresponding brain or cortical activity QEEG index would also rise indicating a higher level of consciousness, wakefulness or awareness than expected.

The schematic also shows in the left center portion 111 of the screen, what is referred to as the trend screen 112 which graphically maps the changes in each hemisphere's calculated QEEG index over time 115. Again, the trend line for each brain hemisphere's brain or cortical activity QEEG index is displayed in color (not shown) corresponding to the displayed QEEG index number, EEG waveform, and electrode lead. This graph serves to map the changes in the brain or cortical activity indices and helps the caregiver to correlate increases in brain or cortical activity with the corresponding EEG waveform. Similar to above, rises in EEG activity shown in the raw waveform would be reflected in the QEEG index relating to brain or cortical activity. However, if it was a momentary or short-lived increase in brain or cortical activity, which may indicate the onset of subject arousal for example, the caregiver might not see it in the real-time QEEG index display. This index map allows the caregiver to see the history of the QEEG index values.

Also displayed in the lower left portion 113 of this schematic is a graphical representation of the measured EMG component 114 of the EEG signal from each brain hemisphere. Again, the EMG signal is displayed in color (not shown) corresponding to the QEEG index display color for the brain hemisphere for which the EMG is recorded. The EMG portion of the signal is recorded and filtered out of the EEG signal so it does not corrupt or intrude on the EEG signal. It is also recorded so that the caregiver can correlate any muscle activity, as reflected in the EMG signal, with increases in the EEG waveform and therefore with the brain or cortical activity indices. It provides a more complete picture of the occurrences leading to any changes in the brain or cortical activity indices that may be registered.

Additionally, electrode information is displayed simultaneously with the above monitoring components in the right center portion 116 of the schematic. The symbol for each electrode is labeled (electrode 1 117, reference 118, ground 119, and electrode 2 120 in this example) and each symbol is displayed in color (not shown) corresponding to the hemisphere of the subject's brain it is recording an EEG signal from. The impedance (electrode 1 121, reference 122, ground 123, and electrode 2 124 in this example) measured for each electrode is also shown in this portion 116 of the display. Also shown are two level bars: one 125 indicating the amount of noise being picked up in the EEG signals, and one 126 representing the percentage of the signal that is artifact corrupted. Together, these components give the caregiver a reference as to how accurate and clear the EEG signal is that is being recorded. The system uses all of the measured and calculated electrode information to make a determination of the electrode or sensor connection and resultant signal quality and displays this determination 127 on the screen.

Figure 8:
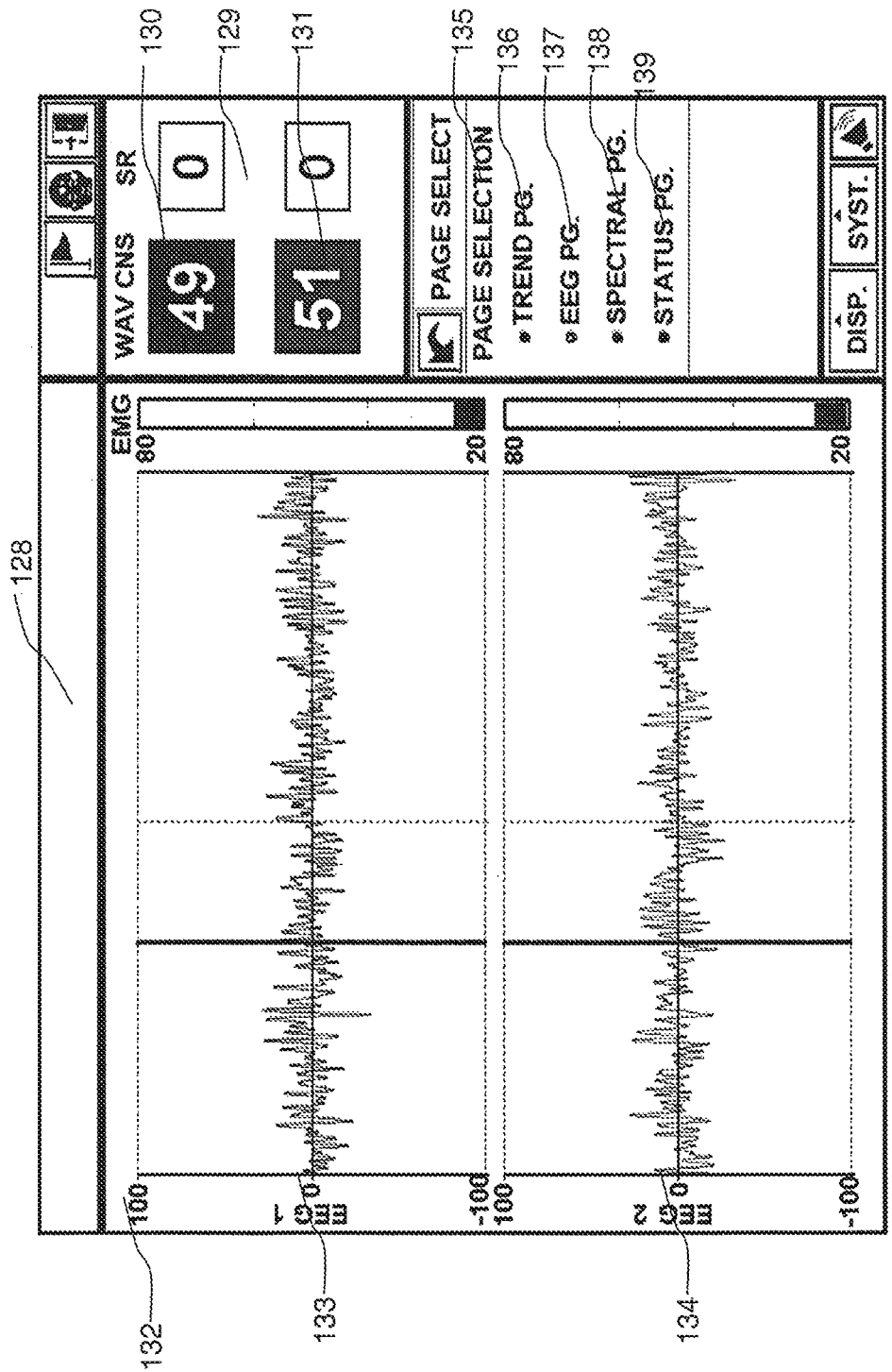
FIG. 8. Image showing QEEG index relating to brain or cortical activity for each of a subject's brain hemispheres along with the corresponding EEG waveforms from each hemisphere.

FIG. 8 is a schematic of another embodiment of the present invention showing the brain or cortical activity indices for each of the subject's brain hemispheres along with the corresponding EEG waveforms in a magnified view. In this display 128, the individual brain or cortical activity indices 130 & 131 for each brain hemisphere are shown in the upper right portion 129 of the display 128 and are preferably displayed in color (not shown) corresponding, as described above, preferably to the electrode lead used (not shown).

On the left portion 132 of the display 128 in this embodiment, the two individual EEG waveforms 133 & 134 are displayed with no other waveform or additional information. The waveform 133 for the right brain hemisphere is displayed on top and in color (not shown) corresponding, as described above, preferably to the electrode lead used (not shown). The waveform 134 for the left brain hemisphere is displayed on top and in color (not shown) corresponding, as described above, preferably to the electrode lead used (not shown).

The lower right portion of the display 128 presents a selection menu 135 which gives the caregiver options for different views or embodiments to employ. The caregiver can select to display a trend page (not shown) by selecting the Trend Page button 136. The caregiver can select to display an EEG waveform page 132 by selecting the EEG Page button 137. The caregiver can select to display a spectral page (not shown) by selecting the Spectral Page button 138. The caregiver can select to display a status page (not shown) by selecting the Status Page button 139. By selecting one of these buttons, the display 128 would be altered to include the selected page.

Figure 9:
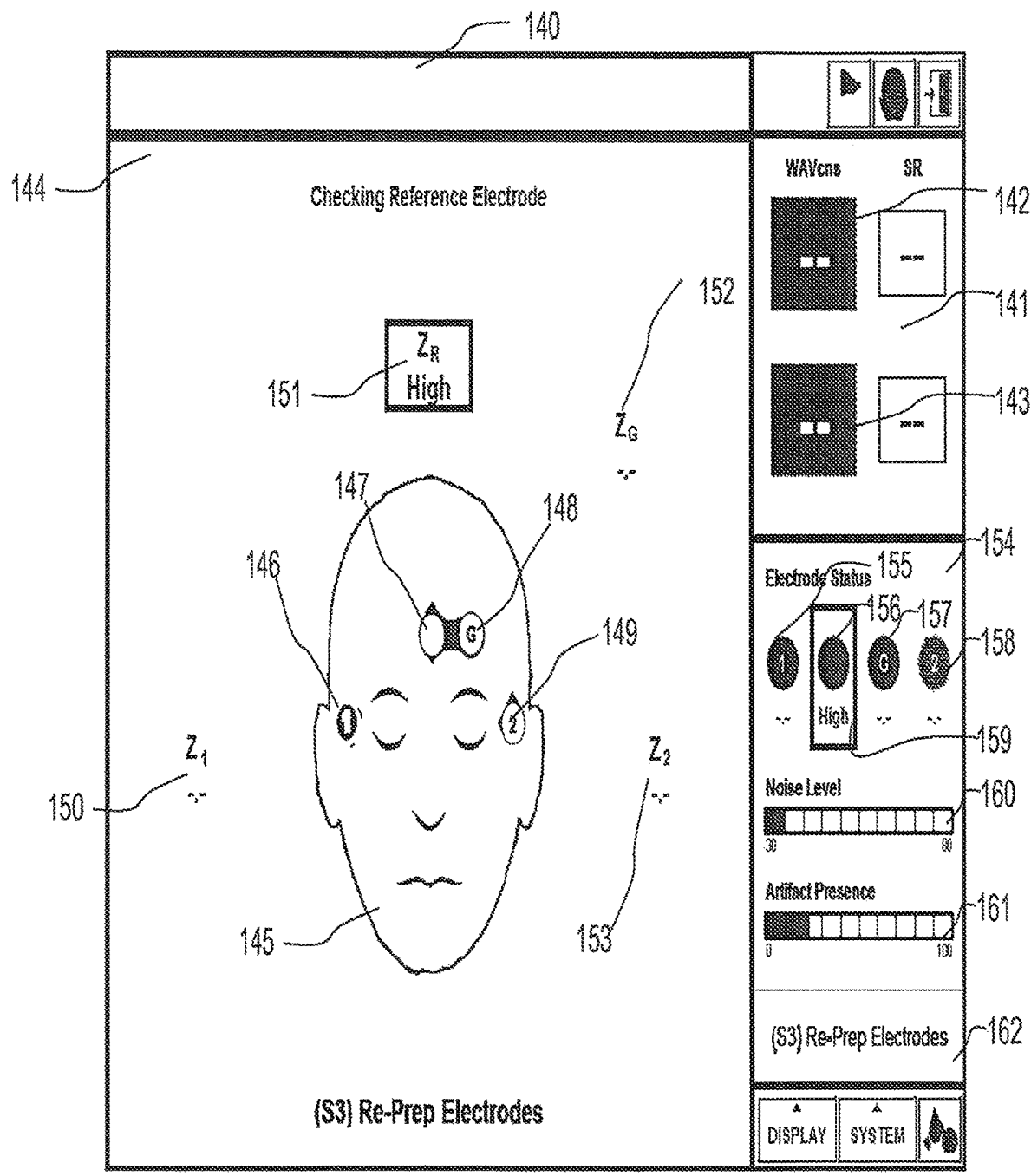
FIG. 9. Image of an electrode impedance and signal quality check with a resulting message indicating that the signal from one of the electrodes is bad due to high electrical impedance.

FIG. 9 is a schematic of another embodiment of the present invention showing an electrode impedance signal quality check process using the bilateral monitoring system and method. In this display 140, although the upper right portion 141 of the display is still shown for the individual brain or cortical activity indices 142 & 143 for each brain hemisphere, the individual brain or cortical activity indices 142 & 143 are not calculated or displayed because there is no EEG signal being transmitted and measured during electrode impedance and signal quality check.

The left portion 144 of the display 140 shows a large representative image of a subject's face 145 with images 146-149 corresponding to the placement of the electrodes used (electrode 1 146, reference electrode 147, grounding electrode 148, electrode 2 149). Also shown on the left portion 144 of the display 140 are the labels 150-153 with measured impedance values corresponding to each electrode 146-149 on the subject's head 145. In this particular embodiment, the reference electrode 147 has been measured and shown to have high impedance, which is displayed on the screen 151. The measurements of the other electrodes 146, 148, 149 are normal and actual measurements are not given 150, 152, 153.

Alternatively, the right center portion 154 of the screen presents another view of electrode signal quality. This signal quality display 154 also gives individual representations 155-158 of the electrodes (electrode 1 155, reference electrode 156, grounding electrode 157, electrode2 158). Additionally, since the measured impedance of the reference electrode 156 was calculated (not shown) to be too high, a visual indicator message 159 is displayed on the screen pointing out that the impedance of that electrode is high. Similar indicators would be shown for any of the other electrodes if necessary. Also shown are two level bars: one 160 indicating the amount of noise being picked up in the EEG signals, and one 161 representing the percentage of the signal that is artifact corrupted. Together, these components give the caregiver a reference as to how accurate and clear the EEG signal is that is being recorded. The system uses all of the measured and calculated electrode information to make a determination of the electrode or sensor connection and resultant signal quality, and instructs 162 the caregiver when attention is required.

Figure 10:
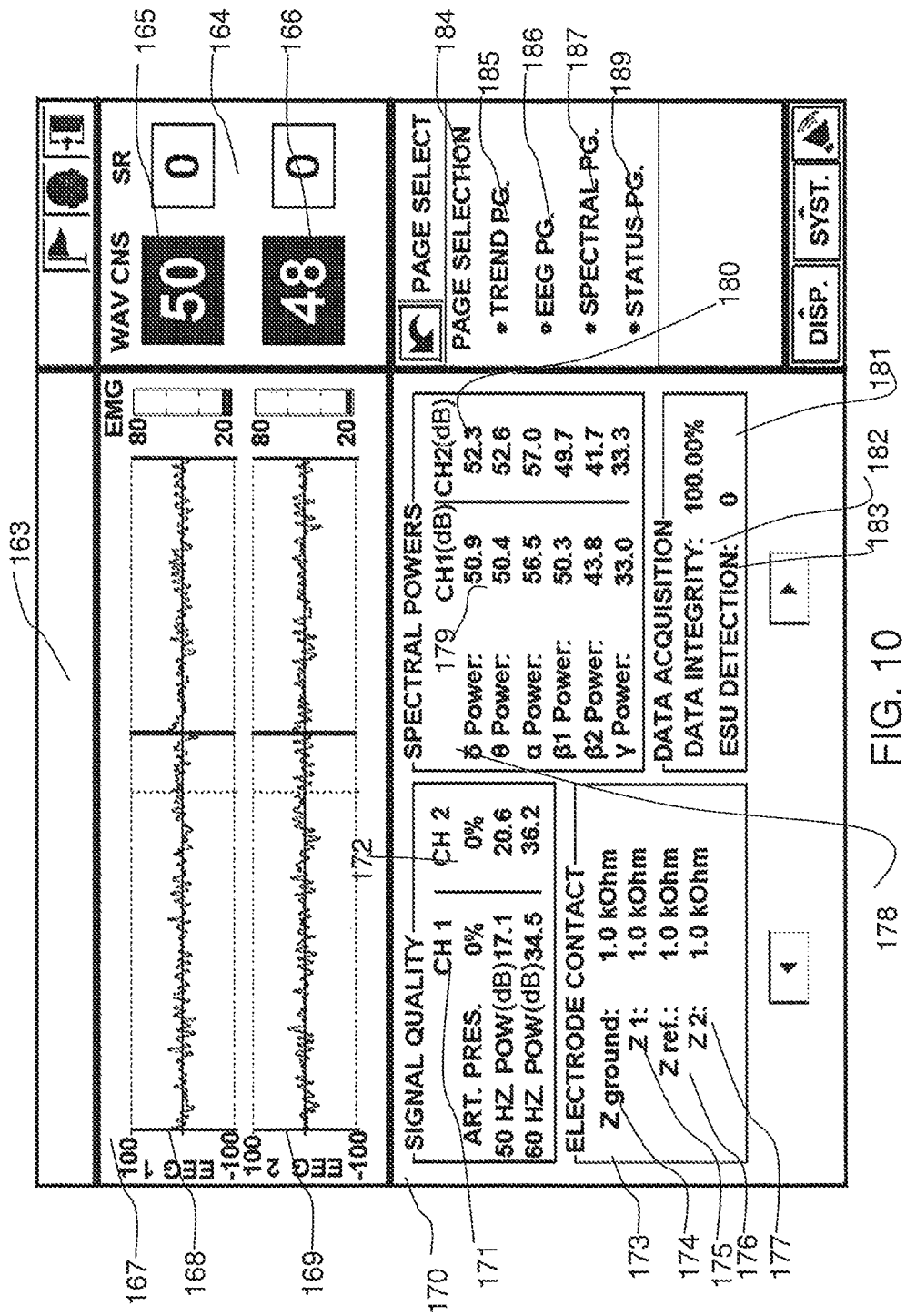
FIG. 10. Image depicting QEEG index relating to brain or cortical activity for each of a subject's brain hemispheres along with the corresponding EEG waveforms from each hemisphere, as well as quantified measurements of electrode signal quality.

FIG. 10 is a schematic of another embodiment of a display showing the two calculated indices and additional information related to the subject being monitored. In this display 163, the individual brain or cortical activity indices 165 & 166 for each brain hemisphere are shown in the upper right portion 164 of the display 163 displayed in color (not shown) corresponding, as described above, preferably to the electrode lead used (not shown).

The individual raw EEG waveforms 168 & 169 for each brain hemisphere are displayed in the upper left portion 167 of the display 163. The waveforms preferably are displayed in color (not shown) matching the color of the corresponding QEEG index 165 & 166 as well as the corresponding electrode (not shown) lead acquiring the given signal. In this embodiment, the right brain hemisphere EEG waveform 168 and QEEG index 165 are displayed in orange while the left hemisphere EEG waveform 169 and QEEG index 166 are displayed in yellow. If a spike is recorded in one of the hemisphere EEG waveforms displayed indicating that some brain or cortical activity has occurred, the corresponding brain or cortical activity QEEG index would also rise indicating a higher level of consciousness, wakefulness or awareness than expected.

A general status page is shown in the lower left portion 170 of the display 163 with various indicator views 170, 175, 180, 183 and measurements displayed simultaneously. This optional view portrays to the caregiver multiple information sources regarding various aspects of the EEG signal acquisition process, all at the same time, rather than choosing one or two display at a given time. Each of these subscreens gives a textual overview of some portion of the EEG signal or measurement process that can be shown in greater detail or in graphical form in some other optional display described in several of the other figures.

One such indicator view is the signal quality portion 171 of the status page 170. This portion displays measurements for both EEG electrodes 171, 172 being collected, each electrode corresponding to one of the subject's brain hemispheres. Various measurements regarding signal quality can be displayed here including, but not limited to, the presence of artifacts in each electrode and the spectral power of each electrode at various frequencies.

Another indicator view is the electrode contact portion 173 of the status page 170. This measurement is closely related to signal quality, but focuses on the fidelity of the connection between the electrodes or other sensors and the subject's body. The system performs this measurement as a function of the electrical impedance of each electrode or sensor. The system then displays the measured impedance value for each of the electrodes or sensors used: grounding electrode 174, first measurement electrode 175, reference electrode 176, and second measurement electrode 177.

Yet another indicator view is the spectral powers measurement portion 178 of the status page 170. This portion displays measurements for both EEG electrodes 179, 180 being collected, each electrode corresponding to one of the subject's brain hemispheres. Various measurements of the spectral powers of the EEG signal from each hemisphere of the subject's brain can be displayed here. The powers of each spectral band or wavelet of the original parent EEG waveform are displayed.

Still another indicator view is the data acquisition portion 181 of the status page 170. This portion displays measurements regarding the quality of the data being recorded by the system from the EEG signal from each hemisphere of the subject's brain. The system can determine the level of data integrity 182 and display that in the data acquisition window, as well as the detection of electrostatic units that may be detected and potentially interfere with the data acquisition and decrease the quality integrity of the recorded data.

The lower right portion of the display 163 presents a selection menu 184 which gives the caregiver options for different views or embodiments to employ. The caregiver can select to display a trend page (not shown) by selecting the Trend Page button 185. The caregiver can select to display an EEG waveform page 132 by selecting the EEG Page button 186. The caregiver can select to display a spectral page (not shown) by selecting the Spectral Page button 187. The caregiver can select to display a status page (not shown) by selecting the Status Page button 189. By selecting one of these buttons, the display 163 would be altered to include the selected page.

Figure 11:
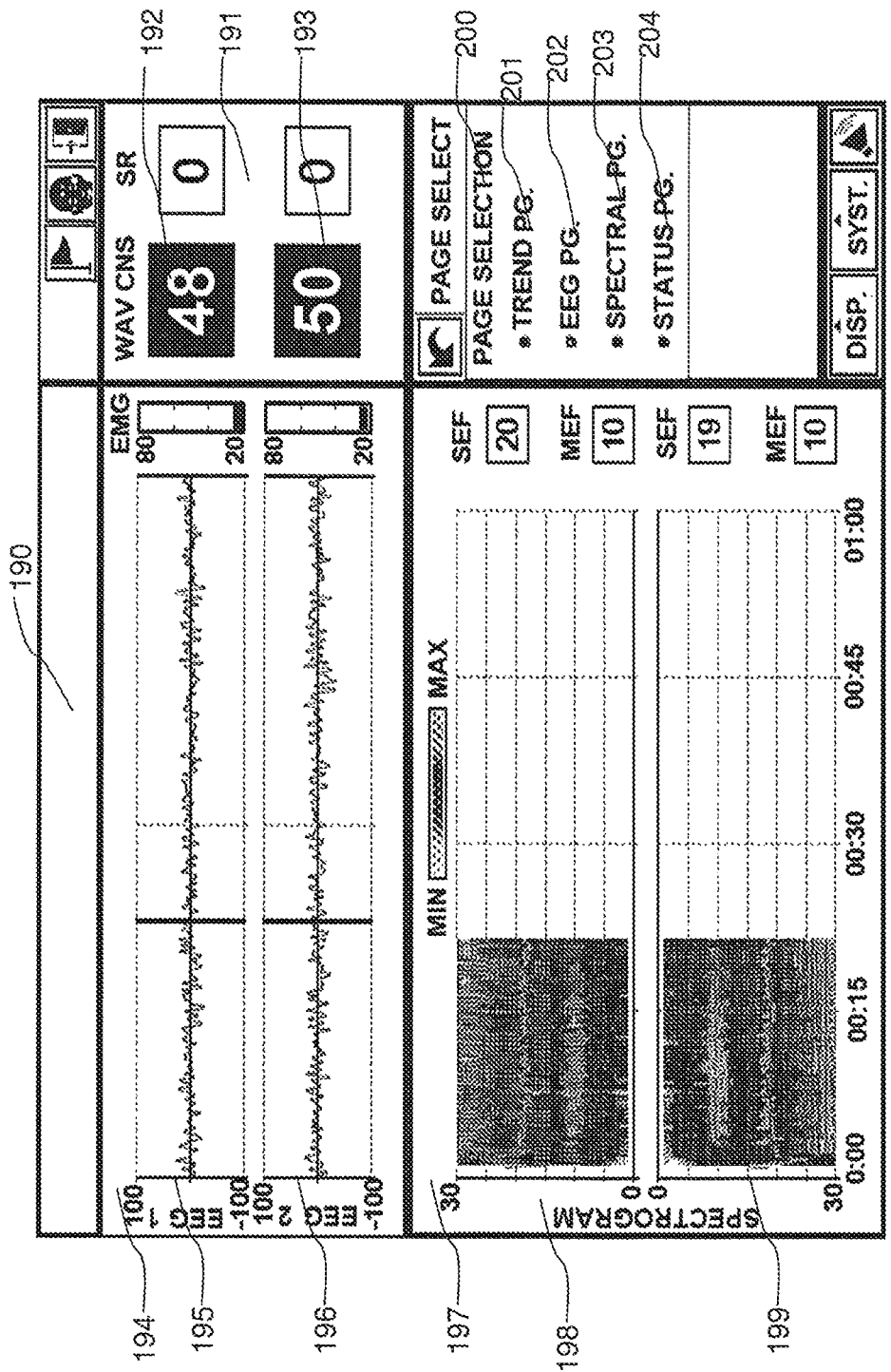
FIG. 11. Image demonstrating brain or cortical activity indices for each of a subject's brain hemispheres along with corresponding EEG waveforms from each hemisphere, and spectral powers graphs of each brain hemisphere's cortical activity.

FIG. 11 is an image of another embodiment of a display showing the two calculated indices and additional information related to the subject being monitored. In this display 190, the individual brain or cortical activity indices 192 & 193 for each brain hemisphere are shown in the upper right portion 191 of the display 190 displayed in color (not shown) corresponding, as described above, preferably to the electrode lead used (not shown).

The individual raw EEG waveforms 195 & 196 for each brain hemisphere are displayed in the upper left portion 194 of the display 190. The waveforms preferably are displayed in color (not shown) matching the color of the corresponding QEEG index 192 & 193 as well as the corresponding electrode (not shown) lead acquiring the given signal. In this embodiment, the right brain hemisphere EEG waveform 195 and QEEG index 192 are displayed in orange while the left hemisphere EEG waveform 196 and QEEG index 193 are displayed in yellow. If a spike is recorded in one of the hemisphere EEG waveforms displayed indicating that some brain or cortical activity has occurred, the corresponding brain or cortical activity QEEG index would also rise indicating a higher level of consciousness, wakefulness or awareness than expected.

The lower left portion 197 of the display 190 presents a spectral powers view of the EEG signals from each of the subject's brain hemispheres. The spectral graphs 198 & 199 corresponding to the EEGs signal from each brain hemisphere are shown in this area when selected by the caregiver in the selection menu 200.

The lower right portion of the display 190 presents a selection menu 200 which gives the caregiver options for different views or embodiments to employ. The caregiver can select to display a trend page (not shown) by selecting the Trend Page button 201. The caregiver can select to display an EEG waveform page 194 by selecting the EEG Page button 202. The caregiver can select to display a spectral page 197 by selecting the Spectral Page button 203. The caregiver can select to display a status page (not shown) by selecting the Status Page button 204. By selecting one of these buttons, the display 190 would be altered to include the selected page.

Figure 12:
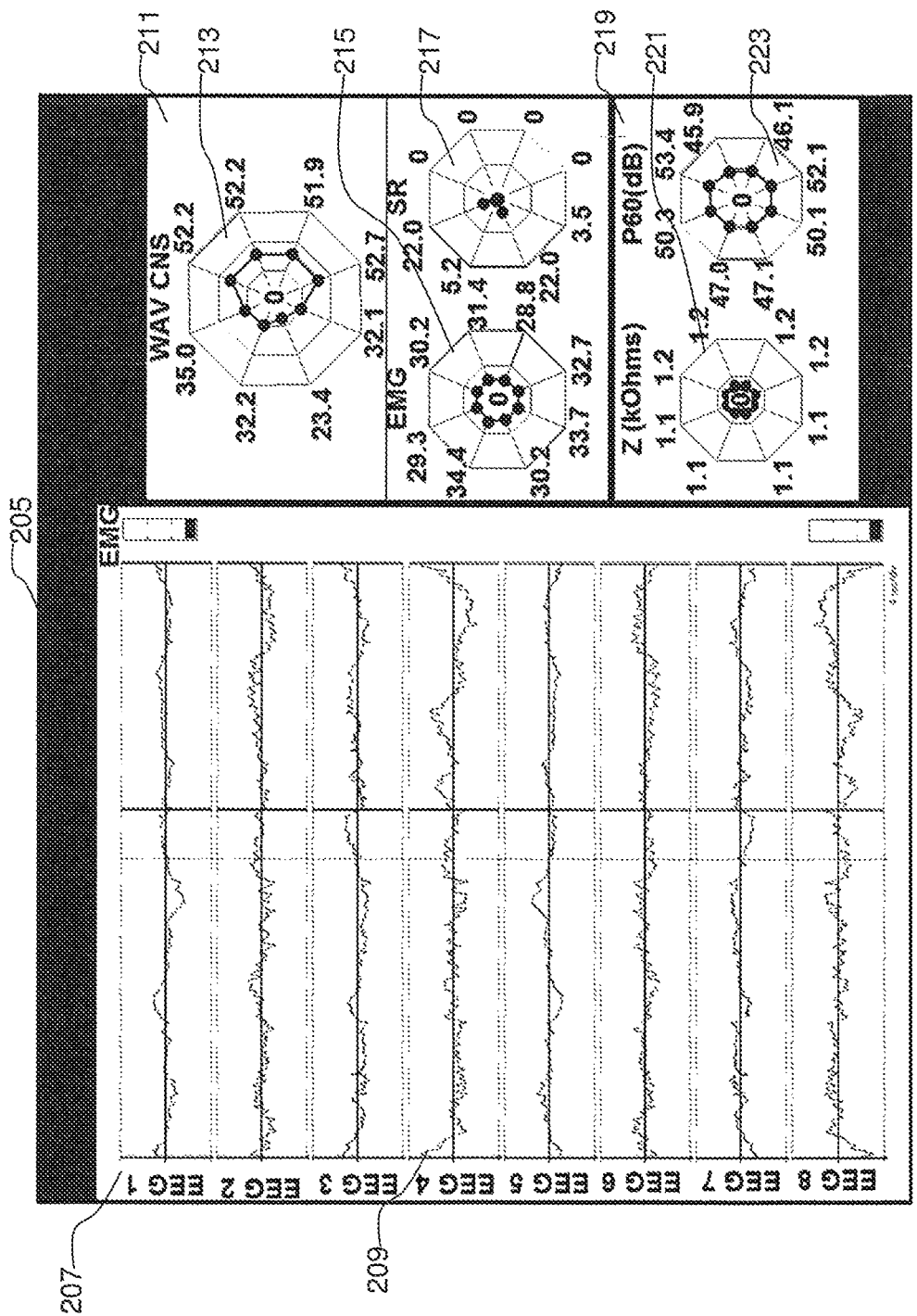
FIG. 12. Image depicting a spider chart of numerous calculated QEEG indices corresponding to various phenomena within the EEG signal.

FIG. 12 is an image of another embodiment of a display showing various EEG waveforms collected from a subject and several spider charts graphically representing data collected from those EEG signals. The display 205 window is divided into separate areas, each providing different information to the user. In the embodiment portrayed in this figure, the left portion 207 of the display 205 is displaying multiple EEG waveforms 209 being collected from the subject. Each EEG waveform 209 represents a separate channel that is connected to the subject. These channels correspond to EEG electrodes (not shown) placed on the subject's head (not shown) which transmit the displayed EEG waveforms 209 to the monitoring equipment and thus to the display 205.

The upper right portion 211 of the display 205 in this particular embodiment displays three spider graphs 213, 215, 217 for the user to see and evaluate. The topmost spider chart 213 depicts the calculated QEEG index for each incoming EEG channel as its calculated value out of a maximum possible value of 100. Also in the upper right portion 211 of the display 205, the lower left spider chart 215 portrays the electromyography (EMG) component measured in each channel of the EEG signal, and the lower right spider chart 217 presents the suppression ratio of each EEG signal corresponding to the length of time during which no substantial EEG signal or brain activity was recorded.

The lower right portion 219 of the display 205 in this particular embodiment portrays two further spider charts. In this portion of the screen, the left spider chart 221 portrays the electrical impedance measured in each of the EEG electrodes attached to the subject. The right spider chart 223 in this embodiment presents the power of the 60 Hz interference (or 50 Hz in, for instance, Europe) measured in each EEG channel attached to the subject and corresponding to the environmental noise.

These spider charts are another display option available to the user to display on the monitor along with options discussed in other embodiments above, all in all providing the user with a robust menu of choices and combinations for displaying many types and varieties of data either individually or in conjunction with each other in numerous embodiments of the present invention.

The invention claims:

1. A method of sedating or anesthetizing a subject by determining electroencephalogram (EEG) signal quality with a device for quantifying brain or cortical activity during sedation or anesthesia comprising steps of:
   a. sedating or anesthetizing a subject;
   b. monitoring the subject with a brain having a left hemisphere and a right hemisphere, the subject under anesthesia or sedation and being monitored with a device for quantifying brain or cortical activity as a function of depth of sedation or anesthesia, the device with at least two EEG measurement electrodes, and at least one EEG reference electrode, the at least two EEG measurement electrodes comprising at least one EEG electrode, for receiving an analog signal, positioned to monitor left hemisphere brain or cortical activity and at least one EEG electrode, for receiving another analog signal, positioned to monitor right hemisphere brain or cortical activity of the subject's brain, each EEG measurement electrode adapted for receiving an EEG analog signal which is subsequently converted to a digital signal;
   c. measuring the brain or cortical activity of both the subject's left and right brain hemispheres essentially simultaneously over a period of time, part of the period of time over which the subject is under sedation or anesthesia;
   d. calculating two numerical quantitative electroencephalogram (QEEG) time-series indices based in part on the digital signals with a processor, the numerical quantitative electroencephalogram (QEEG) time-series indices corresponding to the brain or cortical activity as a function of depth of sedation or anesthesia for each of the subject's left and right brain hemispheres-over the period of time part of which the subject is under sedation or anesthesia;

e. comparing the two numerical quantitative electroencephalogram (QEEG) time-series indices as a function of depth of sedation or anesthesia; and f. treating the subject by administering further sedation or anesthesia to the subject based on comparison, by the processor or with a second processor, of the two numerical quantitative electroencephalogram (QEEG) time-series indices corresponding to the brain activity as a function of depth of sedation or anesthesia for each of the subject's left and right brain hemisphere's.

2. The method of claim 1 wherein an additional step of comparing the quantitative electroencephalogram (QEEG) numerical time-series indices is performed to also determine whether the subject has suffered, or is suffering some neuropathological activity.

3. The method of claim 1 wherein an additional step of comparing the quantitative electroencephalogram (QEEG) numerical time-series indices is performed to also determine if the subject's status has suddenly changed indicating wakefulness or awareness in at least one hemisphere of the subject's brain.

4. The method of claim 2 wherein the device provides a message, either audible and/or visual, notifying a caregiver when the some neuropathological activity is detected.

5. A method of sedating or anesthetizing a subject with a device for quantifying brain or cortical activity in a subject during sedation or anesthesia comprising the steps of:

a. applying at least one electroencephalographic (EEG) measurement electrode at each of a right and a left hemispheric brain regions on the subject, applying at least one EEG reference electrode, and coupling the EEG measurement and reference electrodes to a control and processing system;

b. continuously acquiring an analog electroencephalographic (EEG) signal from each of the EEG measurement electrodes;

c. converting the analog EEG signal from each of the EEG measurement electrodes to a digital EEG signal;

d. separately and concurrently calculating one numerical time-series index for each digital EEG signal representative of the brain activity as a function of depth of sedation or anesthesia for each of the right and left hemispheric brain regions corresponding to the measurement electrodes resulting in two numerical time-series indices;

e. comparing with a processor of the control and processing system the two numerical time-series indices one for each the right and left hemispheric brain regions; and f. administrating a drug or therapeutics for sedation or anesthesia with the processor of the control and processing system based on the comparison.

6. The method of claim 5 wherein an additional step of comparing the two numerical time-series indices is performed to also determine whether the electroencephalographic signal of one or more of the electroencephalographic electrodes is likely to have poor signal quality.

7. The method of claim 5 wherein an additional step of comparing the numerical time-series indices is performed to also determine if the subject's status has changed suddenly indicating wakefulness or awareness.

8. The method of claim 5 wherein the device provides a message, either audible and/or visual notifying a caregiver when a signal quality is low in a given electrode, a neuropathological activity is detected with the subject, or a status changes suddenly with the subject.

9. A processing and control system for sedating or anesthetizing a subject, the processing and control system for quantifying brain or cortical activity in the subject during sedation or anesthesia and adjusting sedation or anesthesia, when necessary comprising:

a. at least two electroencephalogram (EEG) measurement electrodes and an EEG reference electrode, the at least two EEG measurement electrodes adapted for monitoring a subject with a brain having a left hemisphere and a right hemisphere, the at least two measurement electrodes and the EEG reference electrode further adapted for connecting to the processing and control system, the at least two EEG measurement electrodes with one EEG measurement electrode for receiving an EEG signal and adapted to be positioned to monitor the left hemisphere of the brain or cortical activity and the other EEG measurement electrode for receiving an EEG signal and adapted to be positioned to monitor the right hemisphere of the brain or cortical activity of the subject's brain, each EEG measurement electrode adapted when positioned correctly to provide the received EEG signals for each of the respective brain hemispheres;

b. a processor with an algorithm adapted for digitizing the EEG signals and measuring the brain or cortical activity of for each of the subject's left and right brain hemispheres essentially simultaneously and calculating based in part on the digitized signals with the processor at least one numerical quantitative electroencephalogram (QEEG) time-series index corresponding to the brain or cortical activity as a function of depth of sedation or anesthesia for each of the left and right hemispheres of the subject's brain resulting in two numerical time-series indices; and c. a monitor adapted to display the two quantitative electroencephalogram (QEEG) numerical time-series indices corresponding to the brain or cortical activity for each of the left and right hemispheres of the subjects brain simultaneously;

wherein the system is adapted to adjust a device for delivering sedation or anesthesia with the processor in closed loop control based in part on comparing the quantitative electroencephalogram (QEEG) numerical time-series index of each hemisphere's cortical activity as a function of depth of sedation or anesthesia.

10. The system of claim 9 wherein the processor is adapted to measure a change in subject status that corresponds to a reaction of the patient following noxious stimulation.

11. The system of claim 9 wherein the processor is further adapted to compare the two quantitative electroencephalogram (QEEG) numerical time-series indices to also determine whether the signal of one or more of the EEG electrodes is likely to have poor signal quality.

12. The system of claim 9 wherein the processor is further adapted to compare determine the two quantitative electroencephalogram (QEEG) numerical time-series indices to also determine whether the subject has suffered, or is suffering some neuropathological activity.

13. The system of claim 9 wherein the system provides a message, either audible and/or visual notifying a caregiver of a low signal quality in a given electrode, a neuropathological activity is detected with the subject, or a status changes suddenly with the subject.

14. The system of claim 9 where the quantitative electroencephalogram (QEEG) numerical time-series indices are displayed on the monitor in color, that color corresponding to the color of an electrode lead connector, or an electrode label, or an electrode lead wire used to attach the processor to the electrode on that given side of the subject's head.

15. The system of claim 9 where two quantitative electroencephalogram (QEEG) numerical time-series indices corresponding to the brain or cortical activity of the left and right hemispheres are displayed on the monitor simultaneously.

\* \* \* \* \*